United States Patent [19]

Hayakawa et al.

[11] Patent Number: 5,380,874

[45] Date of Patent: Jan. 10, 1995

[54] INTERMEDIATES FOR PYRIDONECARBOXYLIC ACID DERIVATIVES

[75] Inventors: Isao Hayakawa; Shohgo Atarashi, both of Chiba, Japan

[73] Assignee: Daiichi Seiyaku Co., Ltd., Tokyo, Japan

[21] Appl. No.: 205,638

[22] Filed: Mar. 4, 1994

Related U.S. Application Data

[60] Division of Ser. No. 812,830, Dec. 24, 1991, which is a division of Ser. No. 449,160, Dec. 12, 1989, Pat. No. 5,098,912, which is a continuation of Ser. No. 878,023, Jun. 24, 1986, abandoned.

[30] Foreign Application Priority Data

Jun. 26, 1985 [JP] Japan .................................. 60-139830
Dec. 12, 1985 [JP] Japan .................................. 60-279991

[51] Int. Cl.$^6$ ............................................ C07D 207/09
[52] U.S. Cl. ...................................... 548/531; 548/567
[58] Field of Search .............................. 548/531, 567

[56] References Cited

U.S. PATENT DOCUMENTS 4,665,079  5/1987  Culbertson et al. ................ 514/312

*Primary Examiner*—Bernard Dentz
*Attorney, Agent, or Firm*—Burns, Doane, Swecker & Mathis

[57] ABSTRACT

This invention provides novel pyridonecarboxylic acid derivatives having a quite high antimicrobial activity. The derivatives have the following formula:

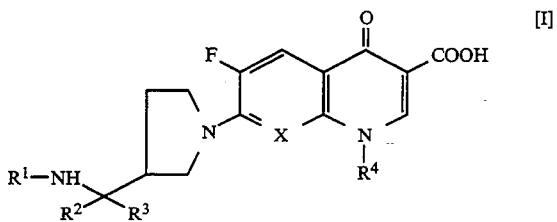

wherein $R^1$, $R^2$ and $R^3$ represent each a hydrogen or $C_1$-$C_6$ alkyl group; $R^4$ represents an ethyl, 2-fluoroethyl, vinyl, isopropyl, isopropenyl or cyclopropyl group; and X represents CH, C—F, C—Cl or N characterized in that $R^2$ and $R^3$ are not hydrogen at the same time.

6 Claims, No Drawings

INTERMEDIATES FOR PYRIDONECARBOXYLIC ACID DERIVATIVES

This application is a divisional of application Ser. No. 07/812,830, filed Dec. 24, 1991, which is a divisional of U.S. application Ser. No. 07/449,160, filed Dec. 12, 1989, now U.S. Pat. No. 5,098,912 issued Mar. 24, 1992, which is a continuation of U.S. application Ser. No. 06/878,023, filed Jun. 24, 1986, now abandoned.

BACKGROUND OF THE INVENTION

1. Field of the Invention

The present invention relates to compounds having a quite high antimicrobial activity and an excellent pharmacokinetics.

2. Prior Art

Intensive investigations have been done heretofore on antimicrobial compounds. Various pyridonecarboxylic acid derivatives are set forth as antimicrobial compounds in the Claims in the specifications of Japanese Patent Public Disclosure (KOKAI) Nos. 67269/1984 (U.S. Ser. No. 416,406) and 214773/1985 (U.S. Ser. No. 581,157). It is disclosed therein that compounds of the general formula:

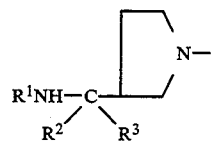

wherein X' represents N, CH or C—F, Y' represents a fluorine and $R^{11}$ represents an ethyl, 2-fluoroethyl or cyclopropyl are preferred. However, compounds of the above general formula in which the basic substituent Z' which exerts a great influenece on the antimicrobial and physicochemical properties represents a pyrrolidine group disclosed heretofore are only those having a group of the formula:

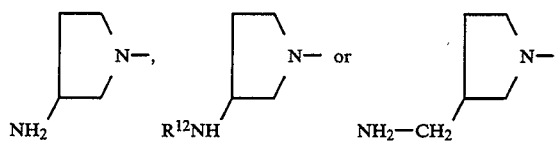

as shown in Example 11 in the specification of J.P. No. 67279/1984 (code No. of the compound: CI-934) and Examples 43 to 47 in the specification of J.P. No. 214773/1985.

However, the actual effect of antimicrobial agents is greatly influenced not only by the antimicrobial activity of the agent, but also by the pharmacokinetics of the agent. In other words, as excellent antimicrobial agent, it is most preferable to use compounds having both strong antimicrobial activity and good pharmacokinetics. It is well-known that the behavior in the human body, i.e., absorbability through the intestinal tract and stability for metabolic disposition depend on physicochemical properties of the compound, in particular, on solubility in water. Namely, if the water-solubility of the compound is extremely low, for example not more than 100 µg/ml, the solubility speed of the compound in the intestinal tract becomes rate-determining, so that the absorption is bad and the compound is easily metabolized when it is absorbed through the intestinal tract.

From thus viewpoint, compound CI-934 has good water-solubility and strong antimicrobial activity against Gram-positive microorganisms, but has a drawback in that its activity against Gram-negative microorganisms is a little weak. On the other hand, the compounds described in examples 44 and 46 of the above J.P. 214773/1985, in which ethyl located on N-1 position of quinoline skeleton is changed to cyclopropyl, have strong antimicrobial activity against Gram-negative microorganisms, but from the extremely low water-solubility thereof it can be assumed that the pharmacokinetics thereof is bad.

SUMMARY OF THE INVENTION

Under such circumstances, the present inventors made various studies and formed that high water solubility can be obtained by selecting compounds of the above formula wherein Z' represents a group of the formula:

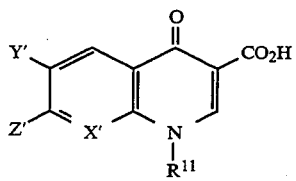

in which at least one of $R^2$ and $R^3$ represents a lower alkyl group and $R^{11}$, X' and Y' represent each a special group from the above-mentioned pyridonecarboxylic acid derivatives, extremely large number of compounds, and in this way there can be obtained compounds having in particular high absorbability through the intestinal tract and stability for metabolic disposition.

It is, therefore, the primary object of the present invention to provide novel compounds having excellent antimicrobial activities against not only Gram-negative and -positive microorganisms but also anaerobes as well as high absorbability through the intestinal tract and stability for metabolic disposition.

Another object of the present invention is to provide a novel process for preparing such compounds.

Another object of the present invention is to provide an excellent antimicrobial agent.

These and other objects of the present invention will be clear from the following description.

In accordance with the present invention, there are provided compounds having the following formula [1]:

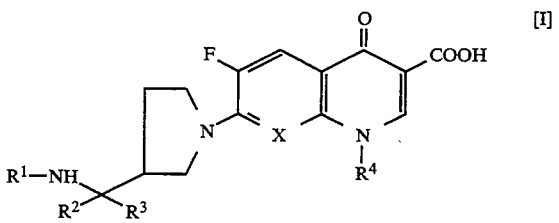

wherein $R^1$, $R^2$ and $R^3$ represent each a hydrogen or alkyl group having 1 to 6 carbon atoms (hereinafter referred to as $C_1$–$C_6$ alkyl group), $R^2$ and $R^3$ being either the same or different and $R^2$ and $R^3$ being not hydrogen at the same time, $R^1$ may form a methylene chain of the formula: $-(CH_2)_n-$ in which n is 2 to 4 together with $R^2$ or $R^3$, or $R^2$ and $R^3$ may form together a methylene chain of the formula: $-(CH_2)_m-$ in which m is 2 to 5; $R^4$ represents an ethyl, 2-fluoroethyl, vinyl, isopropyl, isopropenyl or cyclopropyl group; and X represents CH, C—F, C—Cl or N, and salts thereof.

DESCRIPTION OF THE PREFERRED EMBODIMENTS

Examples of the lower alkyl groups in the general formula [I] include those having 1 to 6 carbon atoms. Examples of the salts of the compounds of the present invention include salts with inorganic acids and organic acids such as hydrochloric acid, sulfuric acid and methanesulfonic acid or with alkali metals and alkaline earth metals such as sodium and calcium. Further, the compounds of the present invention may be in the form of their hydrates. As a matter of course, stereoisomers and optical isomers (L-, D- and racemic compounds) are included in the compounds of the present invention.

$R^1$ in the above general formula [I] for the compounds of the present invention is preferably hydrogen or an alkyl group having 1 to 3 carbon atoms. $R^2$ is preferably hydrogen or an alkyl group having 1 to 3 carbon atoms. $R^3$ is preferably an alkyl group having 1 to 3 carbon atoms. It is also preferred that $R^2$ and $R^3$ form together a methylene chain having 2 to 5 carbon atoms or that $R^1$ and either $R^2$ or $R^3$ form together a methylene chain having 2 to 4 carbon atoms. $R^4$ is preferably ethyl or cyclopropyl and X is preferably CF or N.

The compounds of the present invention can be synthesized by a process wherein a compound of the general formula [II]:

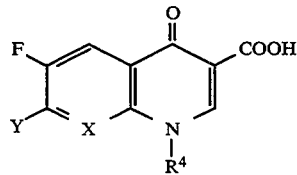

[II]

wherein $R^4$ and X are as defined above and Y represents a halogen atom is reacted with a pyrrolidine derivative of the general formula [III]:

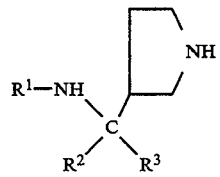

[III]

wherein $R^1$, $R^2$ and $R^3$ are as defined above. This reaction is carried out preferably at a temperature of about 20° to 150° C. in an inert solvent such as acetonitrile, tetrahydrofuran, ethanol, chloroform, dimethyl sulfoxide, dimethylformamide, pyridine, picoline or water.

The pyrrolidine derivative of the above general formula [III] is synthesized by, for example, a process wherein known 1-benzyl-4-carboxy-2-pyrrolidone is treated with thionyl chloride to form an acid chloride, which is then reacted with Meldrum's acid and the resulting product is decarboxylated to obtain 4-acetyl derivative thereof. The ketonic part of the acetyl group is converted into an oxime with hydroxylamine and the product is reduced with lithium aluminum hydride to obtain 3-(1-aminoethyl)-1-benzylpyrrolidine. This product is reacted with 2-[tert-butyloxycarbonyloxyimino]-2-phenyl-acetonitrile (Boc-ON) to form a corresponding tert-butoxycarbonyl (hereinafter referred to as Boc) compound, which is then reduced with palladium/carbon and debenzylated to form 3-(1-tert-butoxycarbonylamino)ethylpyrrolidine. When the Boc compound obtained as above is reduced with lithium aluminum hydride and then with palladium/carbon and debenzylated, 3-(1-methylamino)ethylpyrrolidine is obtained.

In the above-mentioned process for producing the compound of the present invention, the amino group of the pyrrolidine derivative of the general formula [III] may be protected with a group which makes the compound substantially inert to the reaction conditions. Examples of the protective groups include acyl groups such as formyl, acetyl and trifluoroacetyl groups; alkoxycarbonyl groups having 2 to 6 carbon atoms such as ethoxycarbonyl and tert-butoxycarbonyl groups; aryloxycarbonyl groups such as benzyloxycarbonyl, p-methoxybenzyloxycarbonyl and phenoxycarbonyl groups; silyl groups such as trimethylsilyl group; as well as trityl, tetrahydropyranyl, vinyloxycarbonyl, o-nitrophenylsulfenyl, diphenylphosphinyl, p-toluenesulfonyl and benzyl groups. These protective groups can be removed after the reaction, if necessary, by a known process such as hydrolysis with an acid or base.

According to the present invention, at least one of $R^2$ and $R^3$ of the general formula [I] is lower alkyl group, so that strong antimicrobial activity of the compounds can be maintained and at the same time the water-solubility thereof can be increased. As a result, there can be provided compounds having particularly high absorbability through the intestinal tract and stability for metabolic disposition, which are superior to the compound CI-934 in terms of antimicrobial activity against Gram-negative microorganisms. Namely, the compounds of the present invention can be predicted to show good pharmacokinetics and to be low in toxicity, so that the compounds are expected to be valuable as pharmaceutical products.

Therefore, the compounds of the present invention can be used widely as antimicrobial agents to be administered to, for example, human and other mammals orally, parenterally or locally. The present invention will be further illustrated by the following non-limitative examples.

EXAMPLES

The carboxylic acid derivatives (M-1) to (M-3) used as the starting materials in the following examples are as follows:

(M-1): 1-cyclopropyl-6,7,8-trifluoro-1,4-dihydro-4-oxoquinoline-3-carboxylic acid

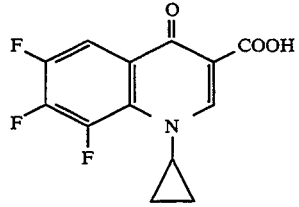

(M-2): 1-ethyl-6,7,8-trifluoro-1,4-dihydro-4-oxoquinoline-3-carboxylic acid

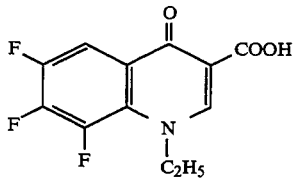

(M-3): 7-chloro-1-cyclopropyl-6-fluoro-1,4-dihydro-4-oxo-1,8-naphthylidine-3-carboxylic acid

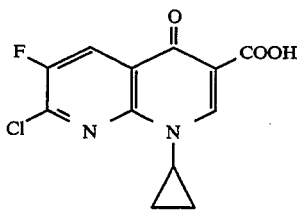

The compounds (M-1) to (M-3) are known ones.

In the following Referential Examples 1 to 23, processes for producing pyrrolidine derivatives to be reacted with the above-mentioned starting compounds will be shown.

Referential Example 1

Synthesis of 1-benzyloxycarbonyl-3-(1-tert-butoxycarbonylaminoethyl)pyrrolidine (P-2):

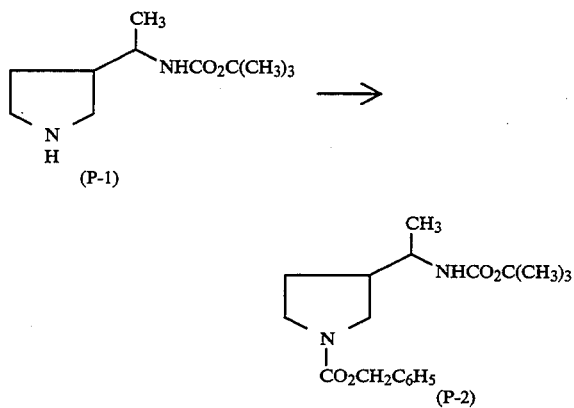

1.5 g of 3-(tert-butoxycarbonylaminoethyl)pyrrolidine (P-1) obtained in Referential Example 25 and 1.0 g of triethylamine were dissolved in 40 ml of tetrahydrofuran. 1.7 g of benzyloxycarbonyl chloride was added dropwise to the solution under cooling with ice and the obtained mixture was stirred at room temperature for 2 h.

The solvent was distilled off and water was added to the residue. After extraction with ethyl acetate, the organic layer was washed with 10% citric acid solution, saturated sodium hydrogencarbonate solution and saturated aqueous sodium chloride solution successively and then dried. The solvent was distilled off and the residue was subjected to column chromatography with 60 g of silica gel to obtain 1.9 g of the desired comound (p-2) as a colorless, viscous oil from a chloroform/methanol (20:1) elute.

NMR(CDCl$_3$)δ: 1.13, 1.18 (each 1.5H, d, J=7 Hz, about 1:1) 1.44(9H, s) 1.6~2.3(3H, m), 2.9~3.8(5H, m), 4.38(1H, d, J=9 Hz) 5.12(2H, s) 7.36(5H, s)

Referential Example 2

Separation of stereoisomers P-2A and P-2B from 1-benzyloxycarbonyl-3-(1-tert-butoxycarbonylaminoethyl)pyrrolidine (P-2) by high performance liquid chromatography (HPLC):

Separation conditions of compound (P-2) by HPLC:

Column: Nucleosil 50-5, 20φ×250 mm
solvent: ethyl acetate/n-hexane (3:1)
flow rate: 5.3 ml/min
retention time: 31.0 min (P-2A), 32.2 min (P-2B)
Isomer (P-2A): IR: 3330, 2970, 1680–1700, 1520 Mass m/e: 349(M$^+$+1) NMR(CDCl$_3$)δ: 1.13(3H, d, J=7 Hz), 1.44(9H, s), 1.7~2.3(3H, m), 2.9~3.9(5H, m), 4.36(1H, d, J=9 Hz), 5.12(2H, s), 7.36(5H, s)
Isomer (P-2B): IR: 3330, 2960, 1680–1670, 1520 Mass m/e: 348(M$^+$) NMR(CDCl$_3$)δ: 1.16(3H, d, J=7 Hz), 1.43(9H, s), 1.6~2.4(3H, m), 2.9~3.9(5H, m), 4.44(1H, d, J=9 Hz), 5.12(2H, s), 7.36(5H, s)

Referential Example 3 i) Synthesis of stereoisomer (P-3A) of 3-(1-tert-butoxycarbonylaminoethyl)pyrrolidine:

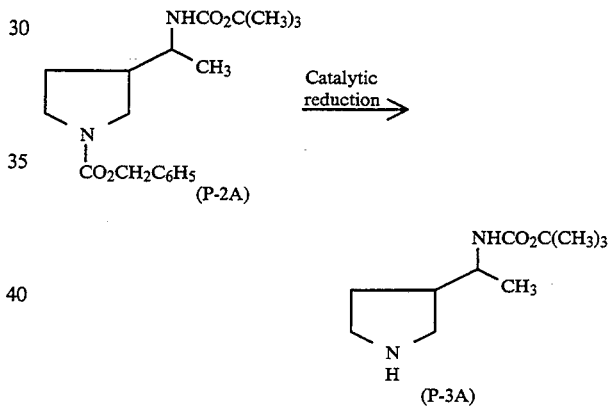

640 mg of 1-benzyloxycarbonyl-3-( 1-tert-butoxycarbonylaminoethyl)pyrrolidine isomer (P-2A) and 300 mg of 5% Pd-C (50% wet) were added to 20 ml of ethanol and catalytic reduction was carried out at room temperature under atm. for 3 h. Then, the catalyst was filtered off and ethanol was distilled off to obtain 390 mg of the desired compound (P-3A) in the form of a colorless, viscous oil.

IR: 1700 (shoulder), 1690 NMR(CDCl$_3$)δ: 1.14(3H, d, J=7 Hz) 1.44(9H, s) 1.5~2.3(3H, m) 2.4~3.3(4H, m) 3.4~3.9(1H, m) 4.56(1H, d, J=9 Hz), ii) Synthesis of stereoisomer (P-3B) of 3-(1-tert-butoxycarbonylaminoethyl)pyrrolidine:

An isomer (P-3B) was obtained in the form of a colorless, viscous oil from the isomer P-2B in the same manner as in Referential Example 3-i).

IR: 1700 (shoulder), 1685 NMR(CDCl$_3$)δ: 1.17(3H, d, J=7 Hz) 1.43(9H, s) 1.7~2.5(3H, m) 2.7~3.4(4H, m) 3.4~3.8(1H, m) 4.83(1H, d, J=9 Hz)

Referential Example 4 i) Synthesis of stereoisomer (P-4B) of 3-(1-methylaminoethyl)pyrrolidine:

[Structures: (P-3B) pyrrolidine with NHBoc, CH3 substituent → LiAlH4 → (P-4B) pyrrolidine with NHCH3, CH3]

346 mg of the isomer (P-3B) was dissolved in 20 ml of anhydrous tetrahydrofuran. 500 mg of lithium aluminum hydride (LiAlH4) was added to the solution and the mixture was refluxed for 1.5 h. After cooling 0.5 ml of water, 0.5 ml of 15% NaOH and 1.5 ml of water were added successively to the mixture and the obtained mixture was stirred for additional 30 min. Insoluble matter was filtered off and the filtrate was concentrated to obtain 180 mg of the desired compound (P-4B) in the form of a light yellow oil.

NMR(CDCl$_3$)δ: 1.06(3H, d, J=6 Hz) 2.39(3H, s)

ii) Synthesis of stereoisomer (P-4A) of 3-(1-methylaminoethyl)pyrrolidine:

An isomer (P-4A) was obtained in the form of an oil from the isomer (P-3A) in the same manner as in Referential Example 4-i).

NMR(CDCl$_3$)δ: 1.02(3H, d, J=6 Hz) 2.39(3H, s)

Referential Example 5

Synthesis of 3-(1-tert-butoxycarbonylaminopropyl)pyrrolidine (P-5):

[Structure: pyrrolidine with NHBoc, C$_2$H$_5$ substituent, labeled (P-5)]

The same procedure as in Referential Examples 24 and 25 was repeated except that ethyl malonate was replaced with ethyl methylmalonate to obtain the desired compound (P-5) in the form of a colorless, waxy, unrefined solid.

NMR(CDCl$_3$)δ: 0.92(3H, t, J=8 Hz) 1.42(9H, s)

Referential Example 6

Synthesis of 2-benzoylamino-2-methylpropionaldehyde (P-6):

[Structure: PhCONH-C(CH3)2-CH2OH → PCC/dry.CH2Cl2 → PhCONH-C(CH3)2-CHO (P-6)]

32.3 g of pyridium chlorochromate (PCC) was added to 200 ml of dehydrated methylene chloride. 50 ml of a solution of 19.3 g of a known compound in the form of an alcohol in dehydrated methylene chloride was added dropwise thereto under stirring over about 1 h and then the stirring was continued for an additional 20 h. Then, 200 ml of anhydrous ether was added thereto and the mixture was stirred for 30 min. The precipitate thus formed was removed by decantation and the obtained solution was decolored by passing through a Florisil column (15 cm). The solvent was distilled off and the residue was purified by silica gel column chromatography to obtain 11 g of the desired aldehyde (P-6) from a chloroform/methanol (10: 1) elute.

NMR(CDCl$_3$)δ: 1.56(3H, s) 6.8(1H, bs) 7.2~8.1(5H, m) 9.4(1H, s)

Referential Example 7

Synthesis of cis- or trans-ethyl 4-benzoylamino-4-methylpentenoate:

4.0 g of the above-mentioned aldehyde (P-6) was dissolved in 60 ml of dehydrated methylene chloride. 20 ml of a solution of 8.0 g of carboethoxymethylenetriphenylphosphorane [(C$_6$H$_5$)$_3$P=COOC$_2$H$_5$] in dehydrated methylene chloride was added dropwise to the solution and the mixture was stirred at room temperature for 6 h. Then, the solvent was distilled off and the residue was subjected to column chromatography with 600 g of silica gel. After elution with benzene/ethyl acetate (2:1), 0.7 g of the desired compound (P-7) in cis-form and 4.5 g thereof in trans-form were obtained each in the form of a colorless powder.

Trans: NMR(CDCl$_3$)δ: 1.34(3H, t, J=7 Hz) 1.6(6H, s) 4.24(2H, q, J=7 Hz) 6.2(1H, bs) 5.9(1H, d, J=16.2 Hz) 7.10(1H, d, J=16.2 Hz) 7.2~7.9(5H, m)

Cis: NMR(CDCl$_3$)δ: 1.20(3H, t, J=7 Hz) 1.72(6H, s) 4.02(2H, q, J=7 Hz) 5.78(1H, d, J=12.6 Hz) 6.36(1H, d, J=12.6 Hz) 7.25~7.95(5H, m)

Referential Example 8

Synthesis of ethyl 4-benzoylamino-4-methyl-3-nitromethylpentanoate (P-8):

[Structures: PhCONH-C(CH3)2-CH=CH-COOC2H5 (P-7) → PhCONH-C(CH3)2-CH(CH2NO2)-CH2-COOC2H5 (P-8)]

2.0 g of the trans-olefin (P-7) and 11.5 ml of tetramethylguanidine were added to 110 ml of nitromethane and the mixture was stirred at room temperature for 20 h. Then, the solvent was distilled off and the residue was dissolved in chloroform. The obtained solution was washed with 0.5N hydrochloric acid and then with saturated aqueous sodium chloride solution and dried over anhydrous sodium sulfate.

Chloroform was distilled off and the obtained oily residue was subjected to column chromatography with 250 g of silica gel. After the elution with chloroform/methanol (20:1), 2.4 g of the desired nitromethane adduct (P-8) was obtained in the form of a colorless powder.

NMR(CDCl$_3$)δ: 1.25(3H, t, J=7 Hz) 1.48 and 1.56 (each 3H, s) 2.4~2.8(2H, m) 4.10(2H, q, J=7 Hz) 4.4~5.0(2H, m) 6.35(1H, bs) 7.2~7.9(5H, m)

The above-mentioned compound can be obtained also from the cis-olefin in a similar manner as described above.

Referential Example 9

Synthesis of 4-(1-benzoylamino-1-methyl)ethyl-2-oxopyrrolidine (P-9):

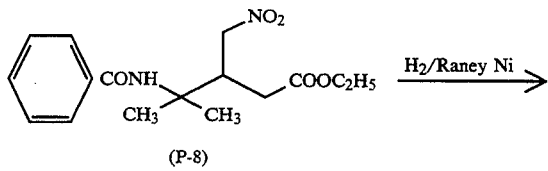

(P-8)

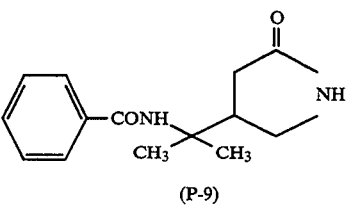

(P-9)

810 mg of the above-mentioned nitro compound (P-8) was dissolved in 40 ml of anhydrous ethanol. Raney nickel was added to the solution and the catalytic reduction was carried out at ambient temperature under atmospheric pressure for 3 days. The catalyst was filtered off and washed with ethanol three times. The wash solutions were added to the filtrate. The residue was subjected to column chromatography with 60 g of silica gel to obtain 50 mg of a pyrrolidone compound (P-9) in the form of a powder from a chloroform/methanol (10:1) elute.

NMR(CDCl$_3$)δ: 1.46(6H, s), 2.1–2.6(2H, m) 2.8~3.8(3H, m), 5.96(1H, bs) 6.16(1H, bs), 7.2–8.0(5H, m)

Referential Example 10

Synthesis of 3-(1-benzylamino-1-methyl)ethylpyrrolidine (P-10):

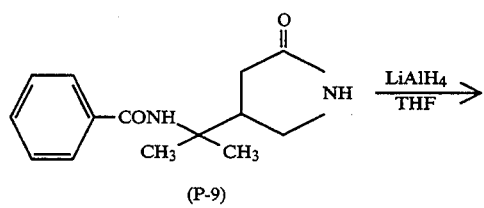

(P-9)

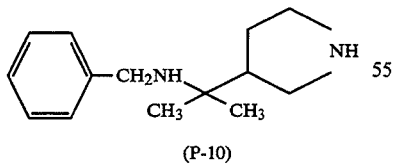

(P-10)

800 mg of lithium aluminum hydride was added to 20 ml of anhydrous tetrahydrofuran containing 780 mg of the above-mentioned amide compound (P-9) . The mixture was refluxed at 80° C. for 6 h. After completion of the reaction, 0.8 ml of water, 0.8 ml of 15% NaOH and 2.4 ml of water were added successively thereto and the mixture was stirred for 30 min. Insoluble matter was removed by filtration and washed with tetrahydrofuran several times. The washing solutions were added to the filtrate and the mixture was concentrated under reduced pressure. The residue was subjected to column chromatography with 60 g of silica gel. After development with n-butanol/acetic acid/water/ethyl acetate (1:1:1:1), the elute was collected and the solvent was distilled off. The obtained residue was dissolved in chloroform, washed with saturated aqueous sodium hydrogencarbonate solution and saturated aqueous sodium chloride solution and dried over anhydrous sodium sulfate. Chloroform was distiled off to obtain 340 mg of the desired compound (P-10).

NMR(CDCl$_3$)δ: 1.12(6H, s), 1.8(2H, m) 2.3(1H, m), 2.9(4H, m) 3.72(2H, s), 7.28(5H, m) 7.25~7.3(2H, m)

Referential Example 10-1

Synthesis of 3-(1-methyl-1-methylamino)ethylpyrrolidine (P-10-1):

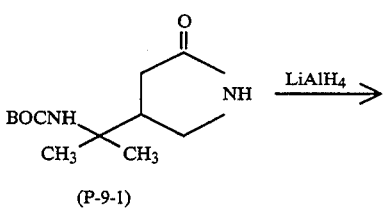

(P-9-1)

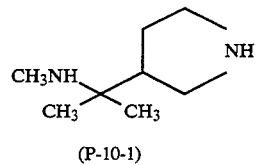

(P-10-1)

The desired compound (P-10-1) was obtained in the same manner as in Referential Example 10 except that a starting material (P-9-1) having BOC in place of benzoyl in the amide (P-9) was used.

Referential Example 11

Synthesis of 3-(1-amino-1-methyl)ethylpyrrolidine (aqueous solution) (P-11):

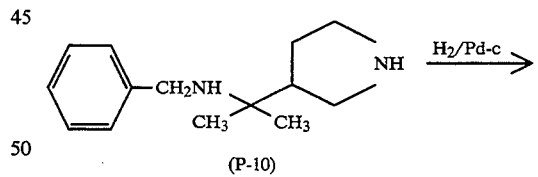

(P-10)

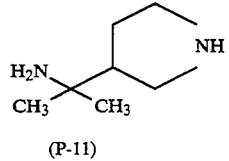

(P-11)

200 mg of the above-mentioned amine (P-10), 200 mg of palladium black and 3 ml of 1N-hydrochloric acid were added to 20 ml of methanol and catalytic reduction was carried out at room temperature under atmospheric pressure for 18 h. After completion of the reaction, 2 ml of 1N-hydrochloric acid was added to the reaction mixture and the catalyst was filtered out. The filtrate was distilled off to obtain hydrochloride of the intended compound (P-11). 3 ml of water and 2 ml of 50% NaOH were added thereto and the mixture was distilled under reduced pressure (bath temperature: about 100° C.) and an aqueous solution of the amine (P-11) distilled was collected using acetone/dry ice refrigerant. 3 ml of water was added to the distillation residue and the same procedure as above was repeated twice to obtain an aqueous solution of amine (P-11), which was used in the subsequent reaction step as it was.

Rf value: 0.20 (n-butanol-acetic acid-water-ethylacetate (1:1:1:1))

Referential Example 12

Synthesis of ethyl 1-tert-butoxycarbonylaminocyclopropanecarboxylate (P-12):

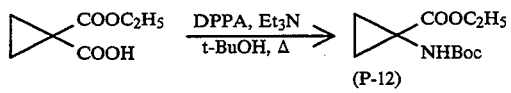

5.0 g of known monoethyl 1,1-cyclopropanedicarboxylate, 4.5 ml of triethylamine and 6.9 ml of diphenyl phosphorazidate (DPPA) were added to 80 ml of tert-butyl alcohol and the mixture was refluxed at 90° to 100° C. for 4 h. After distilling the solvent, the residue was dissolved in ethyl acetate and washed with 5% citric acid, saturated aqueous sodium carbonate solution and saturated aqueous sodium chloride solution and then dried. The solvent was distilled off to obtain 5.7 g of the desired compound (P-12) in the form of a light yellow oil.

NMR(CDCl$_3$)δ: 1.2(7H, m) 1.44(9H, s) 4.12(2H, q, J=7 Hz) 5.04(1H, bs)

Referential Example 13

Synthesis of 1-tert-butoxycarbonylaminocyclopropanecarboaldehyde (P-13):

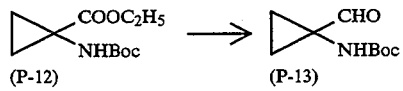

7.1 g of the ester compound (P-12) was dissolved in 200 ml of anyhdrous n-hexane. 46 ml of diisobutylaluminum hydride (1M solution in n-phexane) was added dropwise to the solution under cooling to −65° C. in argon atmosphere and the mixture was stirred at −60° to −70° C. for 4 h. The temperature was elevated to room temperature and the product was extracted sufficiently with saturated sodium hydrogensulfite solution. The precipitate thus formed was filtered off and the aqueous layer was adjusted to pH 9 with 10% NaOH under cooling with ice. After extraction with ether several times, the ether layer was washed with saturated aqueous sodium chloride solution and dried over magnesium sulfate. Ether was distilled off to obtain 2.6 g of the desired aldehyde (P-13) in the form of a colorless solid.

NMR(CDCl$_3$)δppm : 1.36(4H, m), 1.48(9H, s), 5.20(1H, bs), 9.20(1H, s)

Referential Example 14

Synthesis of ethyl 3-(1-tert-butoxycarbonylaminocyclopropyl)acrylate (P-14):

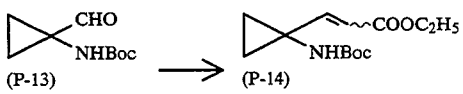

1.12 g of the starting aldehyde was dissolved in 22 ml of anhydrous methylene chloride. 2.24 g of carbethoxymethylene triphenylphosphorane was added to the solution in argon atmosphere and the mixture was refluxed at 60° C. overnight. The solvent was distilled off and the residue was subjected to the column chromatography with 120 g of silica gel to obtain the desired compound (P-14) in mainly trans-form from the elute obtained with benzene/ethyl acetate (2:1). The product was in the form of a white powder.

NMR(CDCl$_3$)δ: 1.30(3H, t, J=7 Hz), 1.40(9H, s), 1.0~1.3(4H, m), 4.20(2H, q, J=7 Hz), 5.0(1H, bs), 5.80(1H, d, J=18 Hz), 6.28(1H, d, J=18 Hz).

Referential Example 15

Synthesis of ethyl 3-(1-tert-butoxycarbonylaminocyclopropyl)-4-nitrobutyrate (P-15):

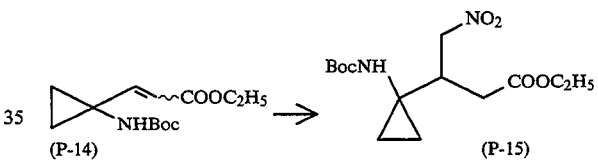

The starting olefin compound (P-14) was dissolved in 60 ml of nitromethane. 4.5 ml of 1,1,3,3-tetramethylguanidine was added to the solution and the mixture was stirred at room temperature overnight. The solvent was distilled off under reduced pressure and the residue was subjected to column chromatography with 100 g of silica gel to obtain 960 mg of the desired compound (P-15) in the form of a colorless oil NMR(CDCl$_3$)δ: 0.85~0.95(4H, m), 1.30(3H, t, J=7 Hz), 1.47(9H, s), 2.25(1H, m), 2.6(2H, m), 4.16(2H, q, J=7 Hz), 4.6(2H, m), 5.0(1H, bs)

Referential Example 16

Synthesis of 4-(1-tert-butoxycarbonylaminocyclopropyl)pyrrolidin-2-one (P-16):

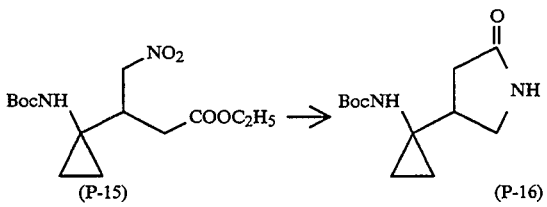

960 mg of the nitro compound (P-15) was dissolved in 50 ml of anhydorus ethanol. Raney nickel was added to the solution and catalytic reduction was carried out at room temperature. The catalyst was removed and ethanol was distilled off. The residue was heated to 150° C.

for 5 min and then subjected to column chromatography with 80 g of silica gel to obtain 320 mg of ring-closed compound (P-16) from chloroform/methanol (10:1) elute. The product was in the form of a colorless powder.

NMR(CDCl₃)δ: 0.7~0.8(4H, m), 1.38(9H, s), 2.3(3H, m), 3.4(2H, m), 5.0(1H, bs), 5.8(1H, bs),

Referential Example 17

Synthesis of 4-(1-aminocyclopropyl)pyrrolidin-2-one trifluoroacetate (P-17):

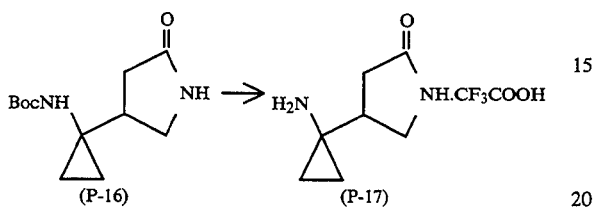

1.2 ml of trifluoroacetic acid and 0.6 ml of anisole were added to 230 mg of the BOC compound (P-16) under cooling with ice and the mixture was stirred at room temperature for 1 h. Then, ether was added to the reaction mixture and the precipitate thus formed was collected by filtration. After thorough washing with ether, 200 mg of the amine trifluoroacetate (P-17) mentioned above was obtained.

Referential Example 18

Preparation of aqueous solution of 3-(1-aminocyclopropyl)pyrrolidine (P-18):

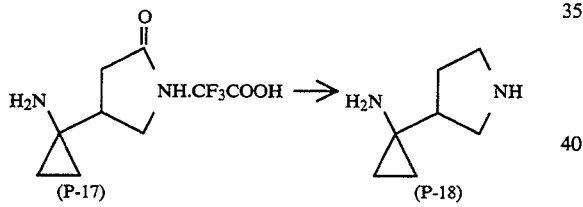

8 ml of tetrahydrofuran was added to 260 mg of the trifluoroacetate (P-17). Then, 0.5 ml of triethylamime was added to the mixture under cooling with ice to dissolve the compound (P-17) therein. 300 mg of lithium aluminum hydride was added to the solution and the mixture was refluxed overnight. 0.3 ml of water, 0.3 ml of 15% NaOH and 0.9 ml of water were added successively thereto under cooling with ice and the mixture was stirred for 30 min. Insoluble matter was filtered off and then 3 ml of 1N-hydrochloric acid was added to the filtrate. The solvent was distilled off under reduced pressure. 3 ml of water and then 3 ml of 50% NaOH were added to the residue under cooling with ice to obtain an alkaline mixture, which was distilled under reduced pressure (oil bath temperature: about 100° C.) and an aqueous solution of the diamine (P-18) thus distilled was cooled and collected in a dry ice/acetone bath.

The aqueous solution of the compound (P-18) thus obtained was used in the subsequent reaction step as it was.

TLC Rf value: 0.14 (n-butanol-acetic acid-water-ethylacetate (1:1:1:1))

The reaction path in the synthesis of the compounds (P-19) to (P-23) is as follows:

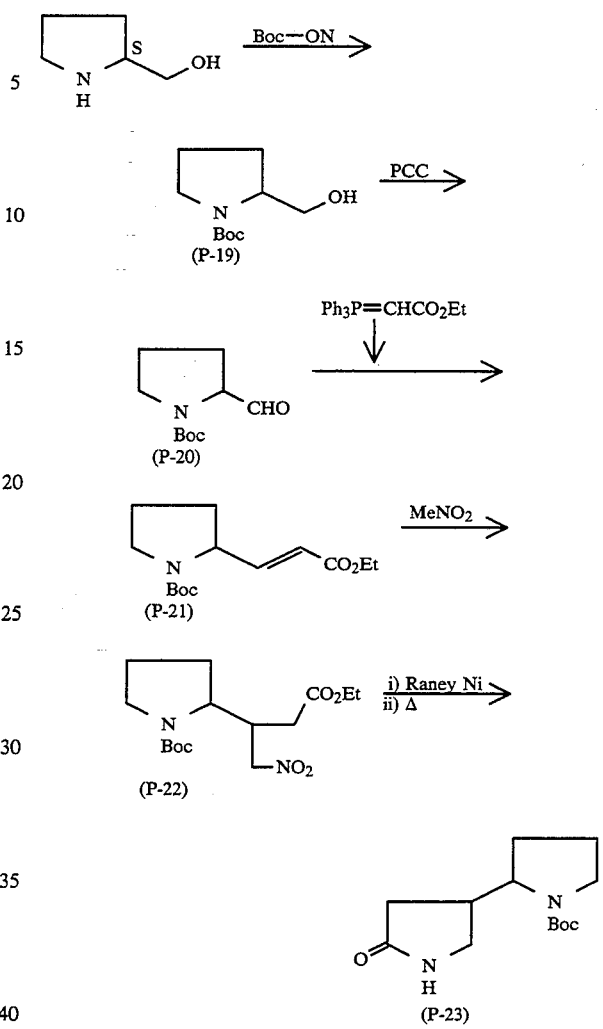

Referential Example 19

Synthesis of (S)-1-tert-butoxycarbonylpyrrolidine-2-methanol (P-19):

4.04 g of (S)-pyrrolidinemethanol and 9.84 g of Boc-ON were dissolved in 100 ml of 75% hydrous dioxane and the solution was stirred for 1 h. Then, the reaction liquid was concentrated, extracted with chloroform, washed with 0.5N-NaOH and saturated aqueous sodium chloride solution and dried over anhydrous sodium sulfate. The solvent was distilled off. The residue was subjected to the column chromatography with 100 g of silica gel and eluted with 2% methanol/chloroform to obtain 8.04 g of a colorless oil (P-19).

Referential Example 20

Synthesis of (S)-1-tert-butoxycarbonylpyrrolidine-2-carboxyaldehyde (P-20):

10 ml of a solution of 8.04 g of the alcohol (P-19) obtained as above in dichloromethane was added to 100 ml of dichloromethane containing 12.9 g of pyridium chlorochromate and the mixture was stirred at room temperature for 2 h. Then, 100 ml of ether was added to the reaction mixture and the mixture was decanted. The residue was washed with 200 ml of chloroform. The wash solution was added to the organic layer and the mixture was passed through a Florisil column to remove chromium compounds. The solvent was distilled off and the residue was purified by column chromatography with 50 g of silica gel and chloroform to obtain 4.76 g (60%) of the aldehyde (P-20) in the form of a yellow oil.

NMR(CDCl$_3$)$\delta$: 1.46(9H, s), 1.70~2.20(4H, m), 3.3~3.6(2H, m), 3.9~4.3(1H, m), 9.4~9.6(1H, bs)

Referential Example 21

Synthesis of ethyl trans-3-(1-tert-butoxycarbonyl-2-pyrrolidinyl)acrylate (P-21):

4.76 g of the aldehyde (P-20) obtained as above and 8.32 g of carbethoxymethylenetriphenylphosphorane were added to 100 ml of dichloromethane and the mixture was heated under reflux for three days. The solvent was distilled off and the residue was subjected to column chromatography with 150 g of silica gel and then eluted with benzene/ethyl acetate (6:1) to obtain 3.83 g of the desired compound (P-21) in the form of a colorless oil.

NMR(CDCl$_3$)$\delta$: 1.28(3H, t, J=7.3 Hz), 1.44(9H, s), 1.6~2.2(4H, m), 3.3~3.55(2H, m), 4.19(2H, q, J=7.3 Hz), 4.3~4.6(1H, m), 5.81(1H, d.d, J=15 Hz), 6.83(1H, d.d, J=15.6 Hz)

Referential Example 22

Synthesis of ethyl 3-(1-tert-butoxycarbonyl-2-pyrrolidinyl)-4-nitrobutyrate (P-22):

3.83 g of the ester (P-21) obtained as above, 3.28 g of 1,1,3,3-tetramethylguanidine and 20 ml of nitromethane were mixed together and the mixture was stirred at room temperature for 24 h. Nitromethane was distilled off and the residue was subjected to the column chromatography with 75 g of silica gel and eluted with benzene/ethyl acetate (5:1) to obtain 4.5 g of the compound (P-22) in the form of a colorless oil.

Referential Example 23

Synthesis of 4-(1-tert-butoxycarbonyl-2-pyrrolidinyl)pyrrolidin-2-one (P-23):

3.30 g of the nitro compound (P-22) and 1.5 ml of Raney nickel were added to 50 ml of ethanol and the catalytic reduction was carried out for a whole day and night. The catalyst was filtered off and the filtratre was concentrated under reduced pressure. 50 ml of benzene was added to the residue and the mixture was refluxed for a whole day and night. Then, benzene was distilled off under reduced pressure and the residue was subjected to the column chromatography with 50 g of silica gel and eluted with chloroform/methanol (95:5) to obtain 2.13 g of the desired ring-closed compound (P-23) in the form of colorless crystals.

m.p. 140°-143° C. NMR(CDCl$_3$)$\delta$: 1.36(9H, s), 1.5~2.2(4H, m), 2.0~2.4(1H, m), 2.9~3.6(4H, m), 3.70~3.96(1H, m)

Referential Example 24

(1) 4-Acetyl-1-benzyl-2-pyrrolidone:

10 ml of thionyl chloride and 30 ml of dioxane were added to 4.4 g of 1-benzyl-4-carboxy-2-pyrrolidone. The mixture was stirred under heating to 90° to 100° C. for 30 min and then the solvent and excess thionyl chloride were distilled off under reduced pressure to obtain and acid chloride residue.

2.5 g of magnesium ethoxide and 3.5 g of ethyl malonate were added to 40 ml of anhydrous ether and the mixture was refluxed for 1.5 h to obtain a solution. The solution of the acid chloride in ether prepared as above was added dropwise to this solution under stirring and under cooling with ice. After completion of the addition, the mixture was refluxed for 1 h. An excess amount of dilute sulfuric acid solution was added thereto under cooling with ice to make the solution weakly acidic. It was extracted with ether and dried.

The solvent was distilled off. 10 ml of acetic acid, 45 ml of water and 1 ml of concentrated sulfuric acid were added to the residue and the mixture was refluxed for 5 h. The solvent was distilled off under reduced pressure. The residue was dissolved in chloroform and washed with 10% hydrochloric acid and then with saturated sodium hydrogen carbonate solution and dried. The solvent was distilled off to obtain 3.3 g of the desired compound in the form of an oil.

NMR(CDCl$_3$)$\delta$ppm: 2.2(3H, s) 2.66(2H, d, J=7.2 Hz) 3.0~3.6(3H, m) 4.32, 4.52(each 1H, d, J=14 Hz, AB-q) 7.29(5H, s)

(2) 1-Benzyl-4-(1-hydroxyiminoethyl)-2-pyrrolidone:

15 ml of pyridine was added to a mixture of 3.3 g of the compound obtained in the above process (1) and 2.5 g of hydroxylamine hydrochloride and the mixture was heated at 90° C. for 5 h. Water was added to the reaction mixture and then it was made acidic with hydrochloric acid and extracted with dichloromethane. Dichloromethane was distilled off and the obtained residue was subjected to column chromatography with 30 g of silica gel. After elution with methanol/chloroform (1:20), 2.6 g of the desired compound was obtained in the form of a powder.

NMR(CDCl$_3$)$\delta$ppm: 1.8(3H, s) 2.62(2H, d, J=7.2 Hz) 2.9~3.6(3H, m) 4.44(2H, s) 7.28(5H, s)

Referential Example 25

(1) 3-(1-Aminoethyl)-1-benzylpyrrolidine:

30 ml of anhydrous tetrahydrofuran (TBF) was added to 650 mg of 1-benzyl-4-(1-hydroxyiminoethyl)-2-pyrrolidone and 500 mg of lithium aluminum hydride and the obtained mixture was reflexed for 20 h. After the decomposition of lithium aluminum hydride, the precipitate was filtered and washed thoroughly with THF. The wash solution was added to the filtrate. The solvent was distilled off under reduced pressure to obtain 587 mg of the desired compound in the form of a light yellow oil.

NMR(CDCl$_3$)$\delta$ppm: 0.1~1.1(3H, 2 pairs of doublet about 1:1, J=7 Hz) 3.55(2H, s) 7.25(5H, s)

(2) 3-(1-tert-Butoxycarbonylaminoethyl)-1-benzylpyrrolidine:

580 mg of the compound obtained in the above step (1) and 730 mg of Boc-ON were dissolved in dehydrated THF and the solution was stirred at room temperature for 3 h. After the starting materials were completely disappeared, TBF was distilled off. Ethyl acetate was added thereto and the mixture was washed with 0.2N NaOH twice and then with saturated aqueous sodium chloride solution once and dried over anhydrous sodium sulfate. The solvent was distilled off and the residue was subjected to the column chromatography with 30 g of silica gel. After elution with 2% methanol/chloroform, 634 mg of the desired compound was obtained in the form of an oil.

NMR(CDCl3)δppm: 1.0~1.2(3H, 2 pairs of doublet, J=7 Hz 1.45(9H, s) 3.6(2H, AB-type quartet) 7.3(5H, s)

(3) 3-[1-(Methylamino)ethyl]-1-benzylpyrrolidine:

642 mg of the compound obtained in the above step (2) and 250 mg of lithium aluminum hydride were added to 10 ml of dehydrated THF and the mixture was refluxed for 2 h. After cooling, 0.25 ml of water, 0.25 ml of 15% aqueous NaOH solution and 0.75 ml of water were added successively thereto and insoluble matter was filtered off. A washer solution of THF (10 ml) was added to the mother liquor and the solvent was distilled off. 448 mg of the desired compound was obtained in the form of a colorless oil.

NMR(CDCl3)δppm: 0.9~1.1(2H, 2 pairs of doublet, J=7 Hz) 2.35(3H, s) 3.55(2H, s) 7.20(5H, s)

(4) 3-[1-(Methylamino)ethyl]pyrrolidine:

20 ml of ethanol and 500 mg of 5% Pd-C (50% wet) were added to 448 mg of the compound obtained in the above step (3) and reduction was carried out at 40° to 50° C. under 4.3 atm. After seven hours, the catalyst was filtered off and the filtrate was concentrated under reduced pressure to obtain 240 mg of the desired compound in the form of a light yellow oil.

NMR(CDCl3)δppm: 0.95~1.15(2H, 2 pairs of doublet, J=7 Hz) 2.39(3H, s)

(5) 3-[1-(tert-Butoxycarbonylamino)ethyl]pyrrolidine:

30 ml of ethanol was added to a mixture of 2.35 g of the compound obtained in the above step (2) and 1.1 g of 5% Pd-C (50% wet) and the reduction was carried out at about 50° C. under 4.3 atm for 4.5 h. The catalyst was removed and then ethanol was distilled off to obtain 1.5 g of the desired compound in the form of a colorless, viscous liquid.

NMR(CDCl3)δppm: 1.42(9H, s) 1.12, 1.15 (each 1.5H, d, J=7 Hz).

Referential Example 26

(12) 4-(1-Aminopropyl)-1-benzyl pyrrolidin-2-one

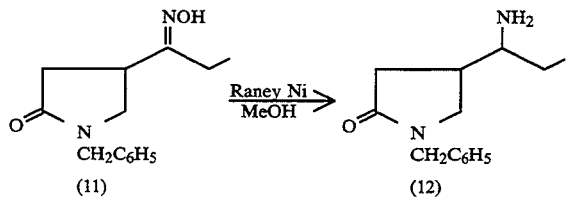

The oxime compound (11) was prepared by the same method as set forth in Referential example 25 except that ethyl methylmalonate was used instead of ethyl malonate. 3.0 g of the oxime compound was dissolved in 30 ml of methanol, after which 4 ml of Raney nickel was added thereto to conduct reduction at room temperature for 24 hours. The catalyst was filtered off and the solvent was distilled off. As a result, 2.8 g (100%) of the amine compound (12) was obtained in the form of a light yellow oil.

NMR(CDCl3)δppm: 0.91(3H, t, J=7 Hz) 1.1-1.5(2H, m), 1.9-2.7(4H, m) 2.9-3.4(2H, m), 4.46(2H, AB-q, J=16 Hz) 7.28(5H, s)

(13) 1-Benzyl-4-(1-tert-butyloxycarbonylaminopropyl)-pyrrolidin-2-one and HPLC separation (compounds 14-A and 14-B)

3.0 g of the amine compound (12) was dissolved in 20 ml of tetrahydrofuran, after which 3.3 g of Boc compound was added thereto, followed by agitating the mixture at room temperature for a whole day and night. The solvent was distilled off and ethyl acetate was added to the residue. The residue was then washed with 10% citric acid, 0.5N -NaOH solution and a saturated NaCl solution, and thereafter was dried. The residue i.e., viscous oil, was subjected to high performance liquid chromatography (HPLC) to separate steric isomers (14-A) and (14-B).

Separating condition

Column: Nucleosil 50-5 (20φ×250 mm)
Solvent: ethyl acetate-tetrahydrofuran (9:1 V/V)
Flow rate: 6.6 ml/min.
Retention time: isomer (14-A): 34 minutes isomer (14-B): 37 minutes Isomer (14-A) 1.4 g (33%) m.p. 123°-124° Elemental analysis calculated for C19H28N2O3: Calculation: C 68.65, H 8.49, N 8.43 Found: C 68.84, 8.51, N 8.37

NMR (CDCl3)δppm: 0.90(3H, t, J=7.5 Hz) 1.1-1:6(2H, m), 1.40(9H, s) 2.1-2.6(3H, m), 2.9-3.7(3H, m) 4.1-4.4(1H, m), 4.43(2H, AB-q, J=16 Hz) 7.28(5H, s)

Isomer (14-B) 1.4 g (33%) m.p. 114°-117° Elemental analysis calculated for C19H28N2O3: Calculation: C 68.65, H 8.49, N 8.43 Found: C 68.88, H 8.49, N 8.49

NMR (CDCl3)δppm: 0.90(3H, t, J=7.5 Hz) 1.0-1.6(2H, m), 1.40(9H, s) 2.0-2.6(3H, m) 2.9-3.6(3H, m) 4.22(2H, AB-q, J=16 Hz) 4.3-4.5(1H, m), 7.28 (5H, s)

Isomer (15-B):
4-(1-Aminopropyl)-1-benzylpyrrolidin-2-one 5 ml of trifluoroacetic acid and 1 ml of anisole were added to 1.3 g of Boc compound (14-B) and then the solution was agitated at room temperature for 30 minutes. The solution was concentrated under reduced pressure, after which water was added to the residure, and the residue was washed, adjusted to alkaline side with NaOH, extracted by chloroform, and dried. 800 mg (88%) of amine compound (isomer 15-B) was obtained in the form of colorless oil.

NMR(CDCl3)δppm: 0.92(3H, t, J=7.5 Hz) 1.1-1.5(2H, m), 1.9-2.7(4H, m) 2.9-3.5(2H, m) 4.45(2H, AB-q, J=16 Hz), 7.28(5H, s)

Isomer (15-A) can also be obtained by a similar procedure as described above.

Isomer (16-B): 3-(1-Aminopropyl)-1-benzylpyrrolidine 800 mg of the amine compound (15-B) was dissolved in 30 ml of tetrahydrofuran, after which 700 mg of lithium aluminum hydride was added thereto and the mixture was heat refluxed for 4 hours. After cooling, 0.7 ml of water, 0.7 ml of 15% NaOH solution and 2.1 ml of water were added to the reaction solution in that order, whereafter the reaction mixture was agitated for 30 minutes, insoluble matter was removed therefrom by filtering, and the filtrate was concentrated. As a result, there was obtained 750 mg (100%) of benzylpyrolidine compound (isomer 16-B) in the form of colorless viscous oil.

NMR(CDCl3)δppm: 0.92(3H, t, J=8 Hz) 1.0-1.7(7H, m), 1.7-2.9(3H, m), 3.60(2H, s), 7.30(5H, s)

Isomer 16-A can also be obtained by a similar procedure as described above.

Isomer 17-B:
1-Benzyl-3-(1-tert-butoxycarbonylaminopropyl)pyrrolidine 750 mg of the benzylpyrrolidine compound (isomer 16-B) was dissolved in 20 ml of tetrahydrofuran, after which 830 mg of Boc-ON compound was added to the solution and the mixture was stirred at room temperature for 1 hour. After the solvent was distilled off, ethyl acetate was added to the residue, and the residue was washed with 0.2N-NaOH solution, with water and dried. The resulting oily product was purified by silica gel chromatography (SiO$_2$ 20 g). As a result, 930 mg (85%) of Boc amine compound (isomer 17-B) was obtained in the form of colorless oil from the fraction eluted with benzene-ethyl acetate (1:1 V/V).

NMR(CDCl$_3$)δppm: 0.90(3H, t, J=8 Hz) 1.1–1.8(4H, m), 1.44(9H, s) 1.8–2.7(5H, m) 3.1–3.5(1H, m), 3.58(2H, AB-q, J=14 Hz) 5.1–5.4(1H, m), 7.30(5H, s)

Isomer (17-A) can also be obtained in the yield of 77% by a similar procedure as described above.

Isomer (18-B):
3-(1-tert-Butoxycarbonylaminopropyl)pyrrolidine 490 mg of benzylpyridine compound was dissolved in 30 ml of ethanol, after which 1.0 g of 5% Pd-C (50% wet) was added thereto and the mixture was subjected to catalytic reduction for 8 hours at a temperature of 40° to 50° C. under a pressure of 4 atoms. After the catalyst was filtrated off, the solvent was distilled off. As a result, 350 mg (100%) of colorless viscous oil (isomer 18-B) containing small amount of crystal was obtained.

NMR(CDCl$_3$)δppm: 0.94(t, J=7 Hz) 1.44(s) , 1.6–2.2(m), 2.8–3.8(m) 4.5–4.8(m)

Isomer (18-A) can also be obtained by a similar procedure as described above.

Example 1

7-[3-(1-tert-Butoxycarbonylaminoethyl)-1-pyrrolidinyl]-1-cyclopropyl-6,8-difluoro-1,4-dihydro-4-oxoquinoline-3-carboxylic acid (isomer A: 1-A-1) was synthesized by the following process:

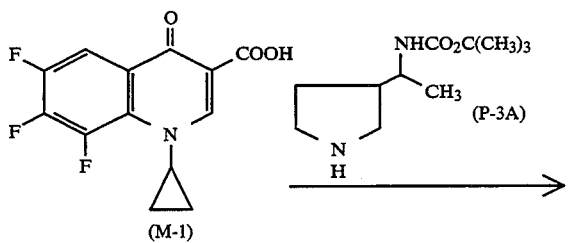

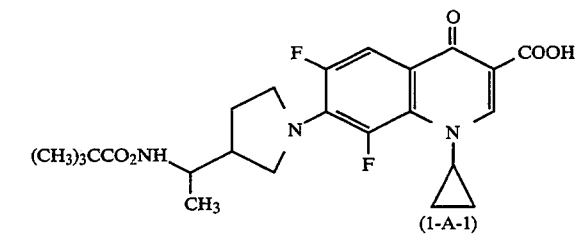

530 mg of 1-cyclopropyltrifluorocarboxylic acid derivatives of formula M-1, 390 mg of an isomer (P-3A) of 3-(1-tert-butoxycarbonylamino-ethyl)pyrrolidine and 190 mg of triethylamine were added to 25 ml of acetonitrile and the mixture was refluxed for 1 h. The solvent was distilled off and water was added to the residue. Insoluble matter was filtered off and the product was washed with acetonitrile and ether successively and dried to obtain 548 mg of the desired compound (1-A-1).

m.p. 195°–198° C. IR: [1725, 1620 NMRδ: 1.22(d, J=7 Hz) 1.1~1.3(m) 1.46(9H, s) 1.5~2.4(3 H, m) 3.4~4.2(6H, m) 4.3~4.6(1H, m) 7.80(1H, dd, J=14 Hz, 2 Hz) 8.73(1H, s)

Elemental analysis calculated for C$_{24}$H$_{29}$F$_2$N$_3$O$_5$
Calculation: C 60.37; H 6.12; N 8.80 Found: C 60.10, H 6.06, N 8.76

7-[3-(1-Aminoethyl)-1-pyrrolidinyl]-1-cyclopropyl-6,8-difluoro-1,4-dihydro-4-oxoquinoline-3-carboxylic acid (isomer A: 1-A-2) compound of the present invention

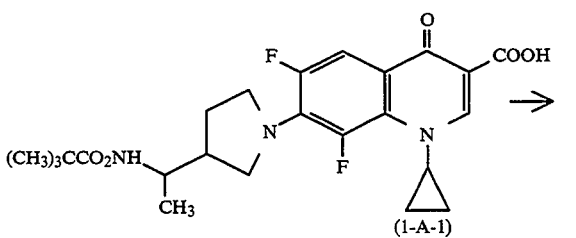

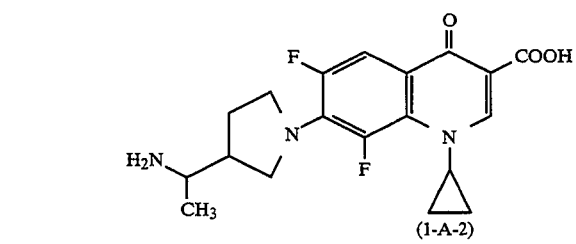

12 ml of trifluoroacetic acid and 4.5 ml of anisole were added to 520 mg of the carboxylic acid (1-A-1) obtained in Example 1-1 and then the mixture was stirred at room temperature for 30 min. The solvent was distilled off, water was added to the residue and the mixture was washed with ether. The aqueous layer was adjusted to pH 8.5 with saturated sodium hydrogencarbonate solution and then neutralized to pH 7.0 to 7.2 with concentrated hydrochloric acid. The aqueous layer was extracted thoroughly with chloroform and dried. Chloroform was distilled off and the resulting solid was recrystallized from concentrated aqueous ammonia/ethanol to obtain 300 mg of the desired carboxylic acid (1-A-2).

m.p. 193°–200° C. IR: 1615, 1580 (shoulder), 1460 NMR(NaOD)δ: 1.05(d, J=6 Hz) 0.9~1.3(m) 1.4~1.7(1H, m) 1.8~2.3(2H, m) 2.74(1H, quintet) 3.2~3.9(5H, m) 7.53(1H, d.d, J=15 Hz, 2 Hz) 8.46(1H, s)

Elemental analysis calculated for C$_{19}$H$_{21}$F$_2$N$_3$O$_3$.5/4-H$_2$O Calculation: C 57.06; H 5.92; N 10.51 Found: C 57.35; H 5.81; N 10.42

Example 2

7-[3-(1-tert-Butoxycarbonylaminoethyl)-1-pyrrolidinyl]-1-cyclopropyl-6,8-difluoro-1,4-dihydro-4-oxoquinone-3-carboxylic acid (isomer B: 1-B-1) was synthesized as follows:

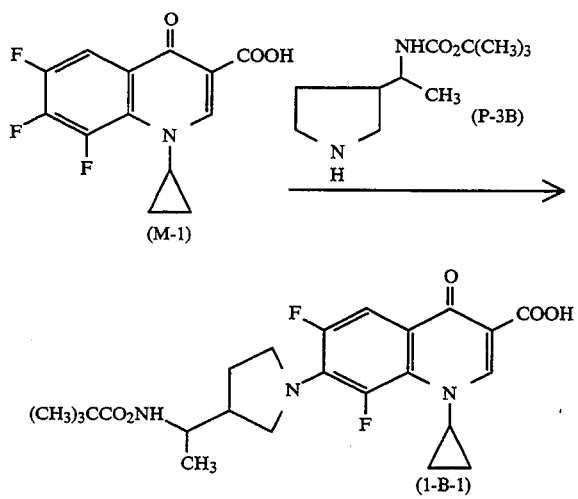

500 mg of 1-cyclopropyltrifluorocarboxylic acid derivative of formula M-1, 350 mg of an isomer (P-3B) of 3-(1-tert-butoxycarbonylaminoethyl)pyrrolidine and 180 mg of triethylamine were added to 20 ml of acetonitrile and the mixture was refluxed for one hour. The solvent was distilled off and then water was added to the residue. Insoluble matter was filtered off. After washing with acetonitrile and then with ether followed by drying, 428 mg of the desired compound (1-B-1) was obtained.

m.p. 201°–204° C. IR: 1720, 1620 NMRδppm: 1.25(d, J=7 Hz) 1.1~1.4(m) 1.45(9H, s) 1.5~2.4(3H, m) 3.5~4.2(6H, m) 4.3~4.6(1H, br.d) 7.80(1H, dd, J=14 Hz, 2 Hz) 8.72(1H, s)

Elemental analysis calculated for $C_{24}H_{29}F_2N_3O_5 \cdot 1/4 H_2O$ Calculation: C 59.80; H 6.17; N 8.72 Found: C 59.82; H 5.81; N 8.41

7-[3-(1-Aminoethyl)-1-pyrrolidinyl]-1-cyclopropyl-6,8-difluoro-1,4-dihydro-4-oxoquinoline-3-carboxylic acid (isomer B: 1-B-2)

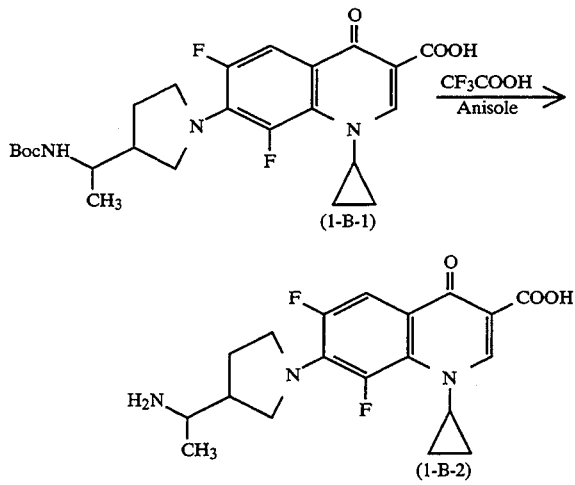

10 ml of trifluoroacetic acid and 1 ml of anisole were added to 410 mg of the carboxylic acid (1-B-1) obtained in Example 2-1 and the mixture was stirred at room temperature for 30 min. The solvent was distilled off and water was added to the residue. After washing with ether, the aqueous layer was adjusted to pH 8.5 with saturated sodium hydrogencarbonate solution, then neutralized to pH 7.0 to 7.2 with concentrated hydrochloric acid and extracted with chloroform. After drying over anhydrous sodium sulfate, chloroform was distilled off and the remaining solid was recrystallized from concentrated ammonia-water/ethanol to obtain 251 mg of the desired compound (1-B-2).

m.p. 213°–215° C. IR: 1615, 1580, 1460
NMR(NaOD)δ: 1.11(d, J=6 Hz) 1.3~1.7(1H, m) 1.9~2.2(2H, m) 2.79(1H, quintet, J=6 Hz) 3.3~4.0(5H, m) 7.57(1H, dd, J=15 Hz, 2 Hz) 8.47(1H, s)

Elemental analysis calculated for $C_{19}H_{21}F_2N_3O_3 \cdot 1/4 H_2O$ Calculation: C 59.76; H 5.67; N 11.00 Found: C 59.79: H 5.90; N 11.02

Example 3

7-[3-(1-Aminoethyl)-1-pyrrolidinyl]-1-ethyl-6,8-difluoro-1,4-dihydro-4-oxoquinoline-3-carboxylic acid (isomer A: 2-A)

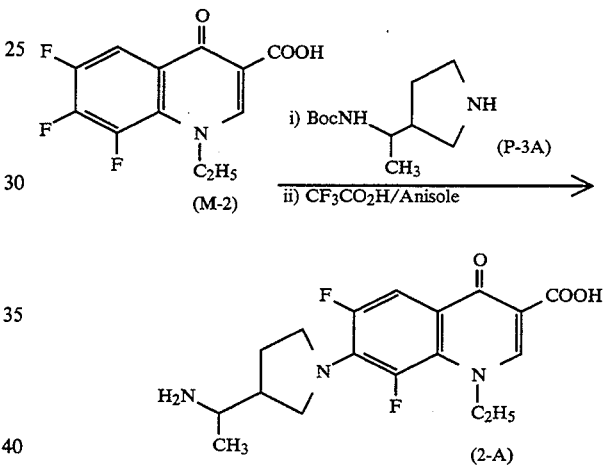

The isomer (2-A) was synthesized in a similar manner as described in the synthesis of an isomer (2-B) in Example 4.

m.p. 212°–215° C. Elemental analysis calculated for $C_{18}H_{21}F_2N_3O_3 \cdot 1/4 H_2O$ Calculation: C 58.45; H 5.86; N 11.36 Found: C 58.40; H 5.71; N 11.41

NMR(NaOD): 1.04(3H, d, J=7 Hz) 1.36(3H, t, J=7 Hz) 1.3~1.6(1H, m) 1.8~2.2(2H, m)

Example 4

7-[3-(1-Aminoethyl)-1-pyrrolidinyl]-1-ethyl-6,8-difluoro-1,4-dihydro-4-oxoquinoline-3-carboxylic acid (isomer B 2-B):

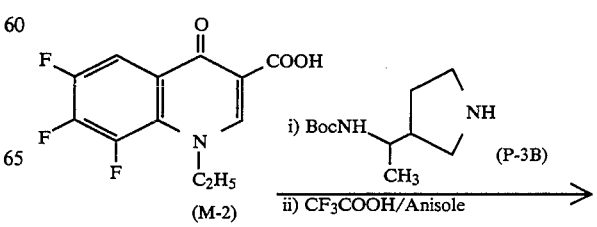

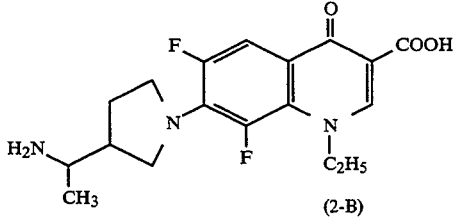

160 mg of 1-ethyltrifluorocarboxylic acid derivative of formula M-2, 166 mg of 3-(1-tert-butoxycarbonylaminoethyl) pyrrolidine (P-3B) and 150 mg of triethylamine were added to 10 ml of acetonitrile and the mixture was heated at a bath temperature of 100° to 110° C. under stirring for 3 h. After cooling, the solvent was distilled off under reduced pressure. The residue was washed with water, ethanol and ether successively and then dried. 0.5 ml of anisole and 5 ml of trifluoroacetic acid were added to the solid and the mixture was stirred at room temperature for about 30 min. Then, the solvent was distilled off under reduced pressure. Water was added to the residue and the mixture was washed with chloroform twice. The aqueous layer was made alkaline with saturated sodium hydrogencarbonate solution, neutralized with concentrated hydrochloric acid, extracted with chloroform three times and dried over anhydrous sodium sulfate. The solvent was distilled off under reduced pressure and the obtained residue was recrystallized from concentrated ammonia-water/ethanol to obtain 105 mg of the desired compound (2-B) in the form of fine crystals.

m.p. 212°–217° C. (Decomposition) Elemental analysis calculated for $C_{18}H_{21}F_2N_3O_3.3/4H_2O$ Calculation: C 57.06; H 5.99; N 11.09 Found: C 57.38; H 6.06; N 11.05

NMR(NaOD)δ: 1.11(3H, d, J=7 Hz) 1.40(3H, t, J=7 Hz) 1.4~1.7(1H, m) 1.9~2.2(2H, m) 2.80(1H, q, J=7 Hz) 3.4~3.9(4H, m) 4.35(2H, m) 7.63(1H, dd, J=16 Hz, 2 Hz) 8.32(1H, s)

Example 5

7-[3-(1-Aminoethyl)-1-pyrrolidinyl]-1-cyclopropyl-6-fluoro-1,4-dihydro-4-oxo-1,8-naphthyridine-3-carboxylic acid:

200 mg of naphthyridinecarboxylic acid derivative of formula M-3 and 150 of 3-(1-tert-butoxycarbonylaminoethyl)pyrrolidine were added to 5 ml of dimethyl sulfoxide and reaction was carried out at 80° C. for 30 min. Then, the solvent was distilled off under reduced pressure. The residue was subjected to column chromatography with 10 g of silica gel and developed with a lower layer of chloroform/methanol/water (15:3:1). 100 mg of anisole and 3 ml of trifluoroacetic acid were added to the obtained Boc compound and the mixture was stirred at room temperature for 30 min. Trifluoroacetic acid was distilled off. Water was added to the residue to obtain a solution, which was distributed by using hexane twice. The aqueous layer was made alkaline with sodium hydrogencarbonate and adjusted to pH 7.4 with hydrochloric acid. After extraction with chloroform three times followed by drying over anhydrous sodium sulfte, chloroform was distilled off. The obtained residue was recrystallized from ethanol to obtain 90 mg of the desired compound.

m.p. 226°–228° C. Elemental analysis calculated for $C_{18}H_{21}FN_4O_3.5/4H_2O$ Calculation: C 56.33; H 5.76; N 14.83 Found: C 56.46; H 6.19; N 14.63

NMR(NaOD)δ: 0.96 and 1.2 (each 2H, m) 1.12(3H, d, J=7 Hz) 1.6 and 2.1 (each 1H, m) 3.3 and 3.5 (each 1H, m) 3.6(1H, m) 3.9(2H, m) 2.8(1H, m) 7.76(1H, d, J=14 Hz) 8.37(1H, s)

Example 6

1-Cyclopropyl-6,8-difluoro-1,4-dihydro-7-[3-(1-methylaminoethyl)-1-pyrrolidinyl]-4-oxoquinoline-3-carboxylic acid (isomer A: 3-A):

This compound was synthesized in a similar manner as described in the synthesis of the isomer (3-B) in Example 7.

m.p. 193°–197° C. Elemental analysis calculated for $C_{20}H_{23}F_2N_3O_3.1/4H_2O$ Calculation: C 60.67s H 5.98; N 10.61 Found: C 60.831H 5.781N 10.61

NMR(NaOD)δ: 1.01(3H, d, J=7 Hz) 0.9~1.3(4H, m) 1.4~1.7(1H, m) 2.0~2.2(2H, m) 2.30(3H, s) 2.4~2.6(1H, m) 3.2~3.9(5H, m) 7.53(1H, dd, J=15 Hz, 2 Hz) 8.46(1H, s)

Example 7

1-Cyclopropyl-6,8-difluoro-1,4-dihydro-7-[3-(1-methylaminoethyl-1-pyrrolidinyl]-4-oxoquinoline-3-carboxylic acid (isomer B: 3-B):

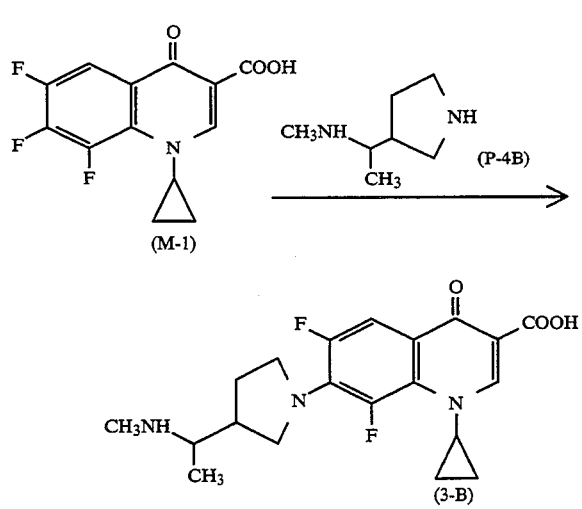

200 mg of compound M-1 was added to 3 ml of dimethyl sulfoxide. The external temperature was elevated to 110° to 120° C. and then 200 mg of 3-(1-methylamino)ethylpyrrolidine (P-4B) was added thereto and the reaction was carried out for an additional 2 h. The solvent was distilled off under reduced pressure and the residue was washed with a small amount of water, ethanol and ether successively and recrystallized from concentrated aqueous ammonia/ethanol to obtain 90 mg of the desired compound (3-B).

m.p. 220°–230° C. (Decomposition) Elemental analysis calculated for $C_{20}H_{23}F_2N_3O_3.1/2H_2O$ Calculation: C 59.991 H 6.04; N 10.49 Found: C 59.74; H 5.79; N 10.45

NMR(NaOD): 1.08(3H, d. J=7 Hz) 0.9~1.3(4H, m) 1.4~1.7(1H, m) 1.9~2.3(2H, m) 2.30(3H, s) 2.4~2.7(1H, m) 3.3~4.0(5H, m) 7.55(1H, dd, J=14 Hz, 2 Hz) 8.46(1H, s)

Example 8

1-Cyclopropyl-6-fluoro-1,4-dihydro-7-[3-(1-methylaminoethyl)-1-pyrrolidinyl]-4-oxo-1,8-naphthyridine-3-carboxylic acid:

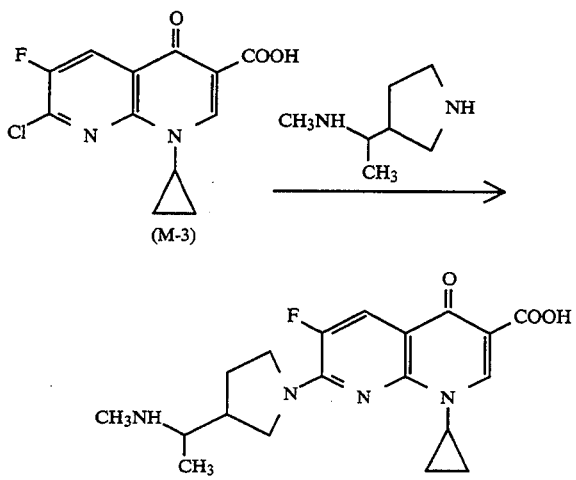

150 mg of starting compound M-3 and 200 mg of 3-(1-methylaminoethyl)pyrrolidine were added to 5 ml of dimethyl sulfoxide and the mixture was maintained at 80° C. for 30 min. The solvent was distilled off under reduced pressure and the residue was subjected to column chromatography with 10 g of silica gel. After elution with a lower layer of chloroform/methanol/water (7:3:1) followed by the recrystallization from ethanol/ether, 85 mg of the desired compound was obtained.

m.p. 199°–202° C. (Decomposition) Elemental analysis calculated for $C_{19}H_{23}FN_4O_3 \cdot 7/4H_2O$ Calculation: C 56.01; H 5.88; N 13.91 Found: C 56.22; H 6.58, N 13.91

NMR(DMSO-d$_6$)δ: 0.9~1.0 and 1.1~1.2 (each 2H, m) 1.04 and 1.08(3H, d) 1.6 and 2.2(2H, m) 2.31(3H, s) 3.0~4.0(5H, m) 7.75(1H, d, J=14 Hz) 8.35(1H, s)

Example 9

7-[3-(1-Aminopropyl)-1-pyrrolidinyl]-1-cyclopropyl-6,8-difluoro-1,4-dihydro-4-oxoquinoline-3-carboxylic acid:

An excess amount of crude 3-(1-tert-butoxycarbonylaminopropyl)pyrrolidine (P-5) and 100 mg of trifluorocarboxylic acid (M-1) were added to 5 ml of dimethyl sulfoxide and the mixture was stirred under heating at a bath temperature of 110° to 120° C. for 30 min. The solvent was distilled off under reduced pressure, whereafter ether was added to the residue and the mixture was stirred and decanted to obtain a precipitate. 2 ml of trifluoroacetic acid and 1 ml of anisole were added to the precipitate and the mixture was stirred at room temperature for 30 min. The solvent was distilled off under reduced pressure. A residue thus obtained was subjected to the column chromatography with 5 g of silica gel. After elution with a lower layer of chloroform/methanol/water (7:3:1), the elute was recrystallized from ethanol/concentrated aqueous to ammonia to obtain 37 mg of the desired compound in the form of light yellow crystals.

m.p. 177°–179° C. Elemental analysis calculated for $C_{20}H_{23}N_3F_2O_3 \cdot 1/4H_2O$ Calculation: C 60.67; H 5.98; N 10.61 Found: C 60.33; H 5.70; N 10.68

NMR(DMSO-d$_6$)δ: 0.92(3H, t, J=7 Hz) 1.25(4H, m) 1.1~1.3(1H, m) 1.3~1.75(2H, d.m) 2.1(2H, m) 3.5~3.95(4H, m) 4.1(1H, m) 8.76(1H, d.d, J=2 Hz, 14 Hz) 8.66(1H, s)

Example 10

7-[3-(1-Aminopropyl)-1-pyrrolidinyl]-1-ethyl-6,8-1,4-dihydro-4-oxoquinoline-3-carboxylic acid:

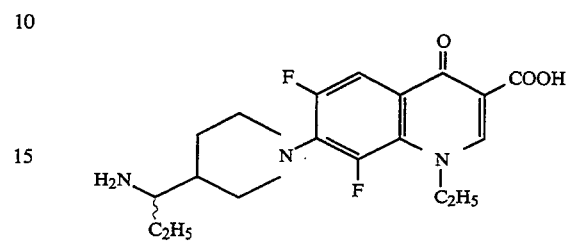

54 mg of the desired compound in the form of light yellow, needle-shaped microcrystals was obtained from 100 mg of compound M-2 in a similar manner as described in Example 9.

m.p. 200°–202° C.

Elemental analysis calculated for $C_{19}H_{23}N_3F_2O_3$ Calculation: C 60.15; H 6.11; N 11.08 Found: C 60.02; H 6.10; N 11.06

NMR(DMSO-d$_6$)δ:0.97(3H, t, J=7 Hz) 1.43(3H, t, J=7 Hz) 1.55(1H, m) 1.70(2H, m) 2.15 and 2.45 (each 1H, m) 3.17(1H, m) 3.5~4.0(4H, m) 4.58(2H, q, J=14 Hz) 7.82(1H, d.d, J=2 Hz, 14 Hz) 8.91(1H; s)

Example 11

7-[3-(1-Amino-1-methyl)ethyl-1-pyrrolidinyl]-1-cyclopropyl-6,8-difluoro-1,4-dihydro-4-oxoquinoline-3-carboxylic acid:

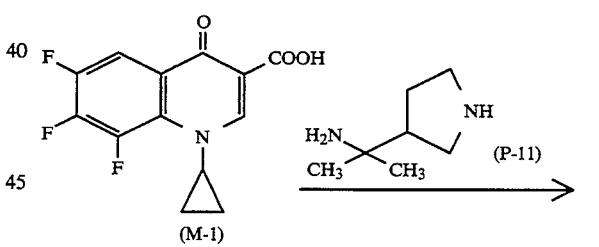

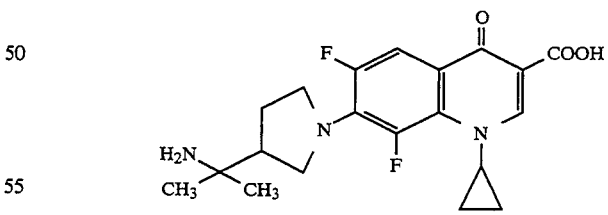

4.5 ml of an aqueous solution containing 100 mg (0.35 mmol) of compound M-1 and at least 2 molar ratio, to the compound M-1, of the amine (P-11) was added to 10 ml of dimethyl sulfoxide and the mixture was stirred under heating at a bath temperature of 150° C. for 40 min. After cooling, the precipitated crystals were collected by filtration, washed with water, ethanol and ether successively. The crystals was treated with active carbon and recrystallized from ethanol to obtain 50 mg of the desired compound in the form of a crystalline powder.

m.p. 227°–230° C. Elemental analysis calculated for C$_{20}$H$_{23}$F$_2$N$_3$O$_3$.1/2H$_2$O Calculation: C 59.99; H 6.04; N 10.50 Found: C 60.02; H 5.98; N 10.47

NMR(NaOD)δ: 0.84~1.32(8H, m) 1.5–2.08(2H, m) 2.20(1H, m) 3.34~4.04(5H, m) 7.57(1H, d, J=14 Hz) 8.47(1H, s)

Example 12

7-[3-(1-amino-1-methyl)ethyl-1-pyrrolidinyl]-1-ethyl-6,8-difluoro-1,4-dihydro-4-oxoquinoline-3-carboxylic acid:

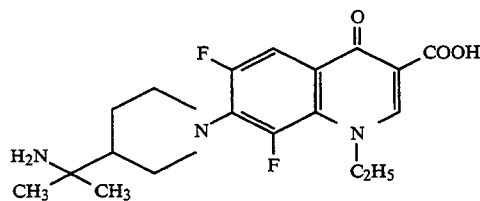

187 mg of the desired carboxylic acid was obtained from 173 mg of the compound M-2 in a similar manner as described in Example 11.

m.p. 235°–240° C. Elemental analysis calculated for C$_{19}$H$_{23}$F$_2$N$_3$O$_3$.H$_2$O Calculation, C 57.42; H 6.34; N 10.57 Found: C 57.38; H 6.07; N 10.47

NMR(NaOD)δ: 1.12(6H, s) 1.40(3H, t, J=8 Hz) 1.70 and 1.96 (each 1H, m) 3.5 and 3.76 (each 2H, m) 4.34(2H, m) 7.64(1H, d, J=14 Hz) 8.32(1H, s)

Example 13

7-[3-(1-Amino-1-methyl)ethyl-1-pyrrolidinyl]-1-cyclopropyl-6-difluoro-1,4-dihydro-4-oxo-1,8-naphthyridine-3-carboxylic acid:

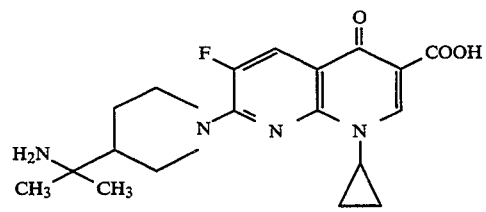

42 mg of the desired carboxylic acid was obtained from 70 mg of compound M-3 in a similar manner as described in Example 11.

m.p. 264°–267° C. Elemental analysis calculated for C$_{19}$H$_{23}$FN$_4$O$_3$ Calculation: C 60.95; H 6.19; N 14.97; Found: C 60.75; H 6.14; N 15.00

NMR(NaOD)δ: 0.96, 1.20 (each 2H×2, m) 1.15(6H, s) 1.5~2.15(2H, m) 2.26(1H, m) 3.3~4.06(5H, m) 7.80(1H, d, J=14 Hz) 8.37(1H, s)

Example 14

1-Cyclopropyl-6,8-difluoro-1,4-dihydro-7-[3-(1-methyl-1-methylamino)ethyl-1-pyrrolidinyl]-4-oxoquinoline-3-carboxylic acid:

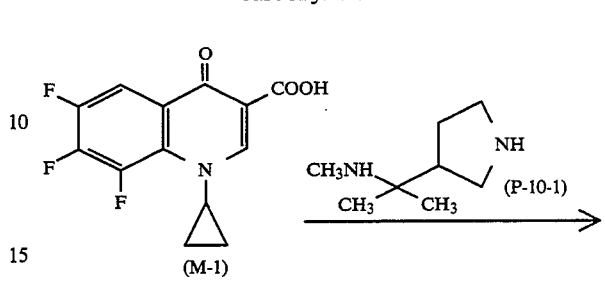

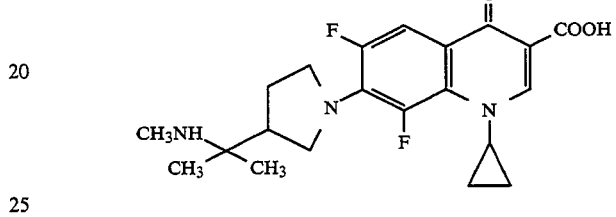

90 mg of compound M-1 and 60 mg of 3-(1-methyl-1-methylamino)ethylpyrrolidine (P-10-1) were added to 5 ml of dimethyl sulfoxide and the reaction was carried out at a bath temperature of 70° for 30 min. Then, the solvent was distilled off under reduced pressure and the residue was subjected to the column chromatography with 10 g of silica gel. After the development with a lower layer of chloroform/methanol/water (7:3:1), the product was recrystallized from ethanol to obtain 55 mg of the desired compound.

m.p. 216°–218° C. (Decomposition) Elemental analysis calculated for C$_{21}$H$_{25}$F$_2$N$_3$O$_3$.1/2H$_2$O Calculation: C 60.86; H 6.32; N 10.14 Found: C 60.65; H 5.99; N 10.07

NMR(NaOD)δ: 1.0~1.2(4H, m) 1.08(6H, s) 2.24(3H, s) 3.60(1H, m) 7.63(1H, d, d, J=14 Hz. and 2 Hz) 8.48(1H, s)

Example 15

7-[3-(1-Aminocyclopropyl)-1-pyrrolidinyl]-1-cyclopropyl-6,8-difluoro-1,4-dihydro-4-oxoquinoline-3-carboxylic acid:

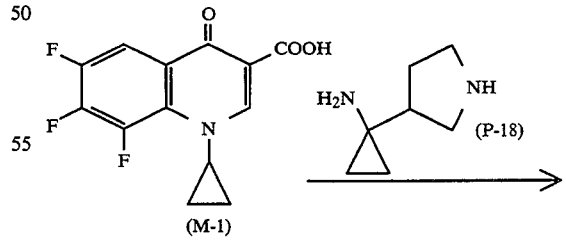

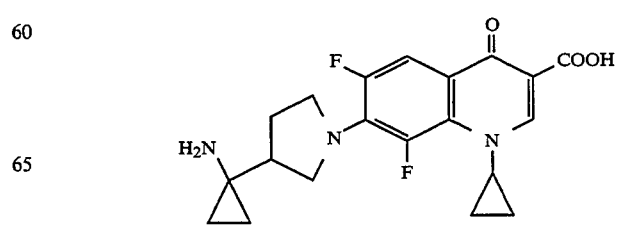

9 ml of an aqueous solution containing 130 mg (0.46 mmol) of the starting compound M-1 and at least two molar ratio, to the compound M-1, of 3-(1-aminocyclopropyl) pyrrolidine (P-18) was added to 20 ml of dimethyl sulfoxide and the mixture was stir red under heating at a bath temperature of 130° to 150° C. for 30 min. After the disappearance of the starting materials was confirmed, the solvent was distilled off under reduced pressure and the residue was subjected to column chromatography with 20 g of silica gel. After the development of the product with a lower layer of chloroform/water/methanol (8:3:1), the product was recrystallized from methanol/chloroform/ether to obtain 52 mg of the desired compound.

m.p. 227°~230° C. NMR(NaOD)δ: 0.92~1.18(4H×2, m) 1.5 & 2.1 (each 1H, m) 2.52(1H, m) 3.1~4.0(2H×2, m) 3.4(1H, m) 7.50(1H, d, J=14 Hz) 8.44(1H, s)

Elemental analysis calculated for $C_{20}H_{21}F_2N_3O_3 \cdot 3H_2O$ Calculation: C 57.68; H 5.81; N 10.09 Found: C 57.31; H 5.66; N 10.39

Example 16

7-[3-(1-aminocyclopropyl)-1-pyrrolidinyl]-1-ethyl-6,8-difluoro-1,4-dihydro-4-oxoquinoline-3-carboxylic acid:

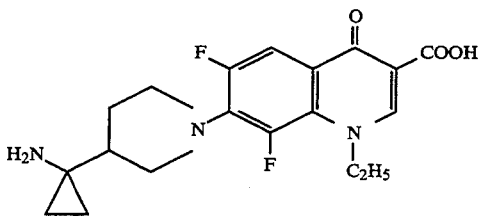

30 mg of the desired carboxylic acid was obtained from 88 mg of compound M-2 in a similar manner as described in Example 15.

m.p. 186°-197° C. Elemental analysis calculated for $C_{19}H_{21}N_3F_2O_3 \cdot H_2O$ Calculation: C 57.71; H 5.86; N 10.63 Found: C 57.90; H 5.81; N 10.49

NMR(NaOD)δ: 0.92~1.18(4H, m) 1.43(3H, t, J=7 Hz) 1.60 and 2.15(2H, m) 2.60(1H, m) 3.4~3.9(4H, m) 4.4(2H, m) 7.75(1H, d, J=14 Hz) 8.33(1H, s)

Example 17

1-Cyclopropyl-6,8-difluoro-1,4-dihydro-7-[3-(2S)-pyrrolidinyl)-1-pyrrolidinyl]-4-oxoquinoline-3-carboxylic acid:

508 mg of the Boc compound (P-23), 10 ml of trifluoroacetic acid (TFA) and 1 ml of anisole were mixed together and the mixture was stirred under cooling with ice for 1 h. TFA was distilled off under reduced pressure and then ether was added to the residue. After decantation, 20 ml of tetrahydrofuran was added to the obtained precipitate, i.e., 3-(2S)-pyrrolidinylpyrrolidin-2-one trifluoroacetate (P-24-1). 500 mg of lithium aluminum hydride was added thereto under cooling with ice and the mixture was heated under reflux for 2 h. 2 ml of water was added dropwise thereto under cooling with ice and insoluble matter was filtered off. The filtrate was concentrated to dryness to obtain a colorless oil, i.e., 3-(2S)-pyrrolidinylpyrrolidine (P-24-2). 1 ml of dimethyl sulfoxide and 100 mg of 6,7,8-trifluorocarboxylic acid (M-1) were added to the crude compound (P-24-2) and the mixture was maintained at 120° C. under stirring for 10 min. The solvent was distilled off under reduced pressure. Ethanol was added to the residue and 50 mg of thus formed, yellow crystals were collected by filtration, dissolved in ethanol and aqueous ammonia, treated with active carbon and recrystallized to obtain 18 mg of the desired compound in the form of colorless crystals.

m.p. 284°-287° C. Elemental analysis calculated for $C_{21}H_{23}N_3O_2F_2 \cdot 1/2H_2O$ Calculation: C 61.16; H 5.87; N 10.19 Found: C 61.371 H 5.63; N 10.17

NMR (NaOD)δ: 0. 90~1.40(4H, m) 2.6~3.0(1H, m) 7.54(1H, d, J=14 Hz) 8.46(1H, s) Others 1.40–210(6H, m), 3.30~3.90(6H, m)

Example 18

7-[3-(1-Aminoethyl)-1-pyrrolidinyl]-1-1-cyclopropyl-6-fluoro-1,4-dihydro-4-oxo-1,8-naphthyridine-3-carboxylic acid (isomer P-25)

180 mg of isomer P-25 was obtained by the same reaction as set forth in Example 1 except that 400 mg of compound M-3 and 420 mg of amine compound (P-3A) were used.

m.p. 225°-226° C. Elemental analysis calculated for $C_{18}H_{21}FN_4O_3 \cdot 3/2H_2O$ Calculation: C 55.81; H 6.24; N 14.46 Found: C 56.05; H 6.26; N 14.15

NMR(NaOD)δ(ppm): 0.8-1.2(4H, m) 1.05(3H, d, J=6.3 Hz) 7.63(1H, d, J=13.5 Hz) 8.29(1H, s)

Example 19

Isomer P-26 was obtained by the same procedure as set forth in Example 18.

m.p.: 255°-255° C. Elemental analysis calculated for $C_{18}H_{21}FN_4O_3 \cdot H_2O$ Calculation: C 57.82; H 6.07; N 14.98 Found: C 57.93; H; 6.32; N 14.67

NMR (NaOD)δ(ppm): 0.8-1.2(4H, m), 1.09(3H, d, J=6.3 Hz) 7.62(1H, d, J=13.5 Hz), 8.28(1H, s)

Example 20

Isomer (P-27):
1-ethyl-6,8-difluoro-7-[3-(1-aminopropyl)-1-pyrrolidinyl]-1,4-dihydro-4-oxoquinoline-3-carboxylic acid

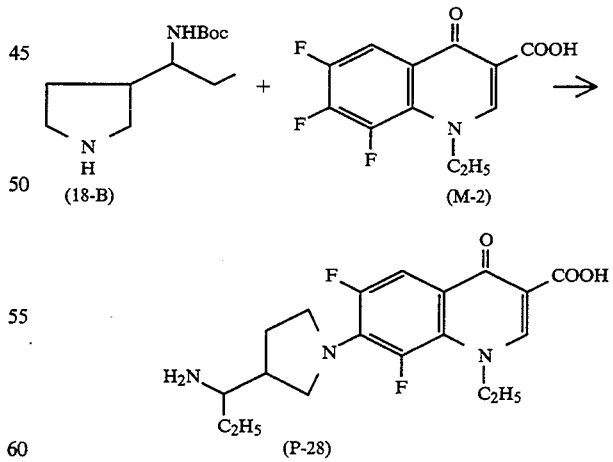

200 mg of compound M-2 was suspended in a mixed solution of 20 ml of acetonitrile and 160 mg of triethylamine, after which 190 mg of pyrrolidine compound 18-B was added thereto and the mixture was refluxed for 3 hours. After the solvent was distilled off, water was added to the residue and the insoluble matter was collected by filtration, washed with water, acetonitrile and ether in that order, and dried. The thus obtained colorless crystal was added to a mixed solution of 5 ml of trifluoroacetic acid and 0.5 ml of anisole and the solution was stirred at room temperature for 30 minutes.

After concentration, water was added to the resulting residue. The mixture was washed with chloroform and adjusted to pH 10-11 with 1N sodium hydroxide. After adjusting to pH 7.06 with 10% citric acid, the solution was extracted three times with chloroform. The extract was concentrated to about 3 ml and ether was added thereto. As a result, 127 mg (45%) of isomer (P-27) was obtained in the form of colorless crystal.

m.p.: 211°–215° Elemental analysis calculated for $C_{19}H_{23}F_2N_3O_3 \cdot 1/2H_2O$ Calculation: C 58.75, H 6.23, N 10.82 Found: C 58.37, H 5.87, N 10.68

NMR (NaOD)δppm: 0.94(3H, t, J=6 Hz) 1.43(3H, t, H=6 Hz), 1.2–1.9(3H, m) 1.9–2.3(2H, m) 2.5–2.7(1H, m), 3.4–3.9(4H, m) 4.2–4.5(2H, m) 7.70(1H, dd, J=15 Hz), 8.32(1H, s)

Example 21

Isomer (P-28):
1-Cyclopropyl-6,8-difluoro-7-[3-(1-aminopropyl)-1-pyrrolidinyl]-1,4-dihydro-4-oxoquinoline-3-carboxylic acid

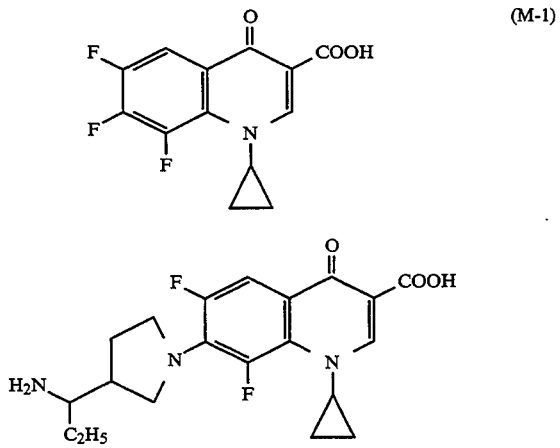

160 mg of isomer (P-28) was obtained by a similar procedure as set forth in Example 20, except that 250 mg of compound M-1 instead of compound M-2 was used and 150 mg of triethyl amine and 250 mg of pyrrolidine compound (18-B) were used.

m.p.: 205°–208° Elemental analysis calculated for $C_{20}H_{23}F_2N_3O_3 \cdot 1/4H_2O$ Calculation: C 60.67, H 5.98, N 10.61 Found: C 60.34, H 5.75, N 10.58

NMR (NaOD)δppm: 0.94(3H, t, J=6 Hz), 1.0–1.25(4H, m) 1.25–1.8(3H, m) 1.9–2.3(2H, m) 2.55–2.7(1H, m), 3.3–4.1(5H, m) 7.64(1H, dd, J=15 Hz) 8.48(1H, s)

Example 22

Isomer P-29 was obtained by a similar procedure as set forth in Example 19.

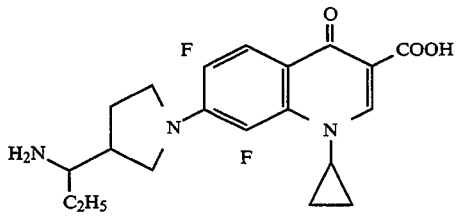

m.p. 166°–168° C. Elemental analysis calculated for $C_{20}H_{23}F_2N_3O_3 \cdot 2/2H_2O$ Calculation: C 57.41, H 6.26, N 10.04 Found: C 57.56, H 6.06, N 10.10

NMR (NaOD)δppm: 0.93(3H, t, J=6 Hz) 1.0–1.2(4H, m) 1.2–1.4(1H, m), 1.4–1.7(2H, m) 1.9–2.3(2H, m) 1.9–2.65(1H, m), 3.3–4.0(5H, m) 7.60(1H, dd, J=15 Hz, 2 Hz), 8.46(1H, s)

The antimicrobial activities of the compounds of the present invention were determined according to a standard process designated by the Japan Society of Chemotherapy and the minimum growth inhibitory concentrations (MIC) (μg/ml) of the compounds were determined. The results are summarized in the following table. Comparative compounds used were as follows:

(A): Compound in Example 44 in J.P. No. 214773/1985; 1-cyclopropyl-6,8-difluoro-(3-ethylaminomethyl-1-pyrolidinyl)-1,4-dihydro-4-oxoquinoline-3-carboxylic acid.

(B): Compound in Example 46 in J.P. No. 214773/1985; 1-cyclopropyl-6,8-difluoro-(3-methylaminomethyl-1-pyrolidinyl)-1,4-dihydro-4-oxoquinoline-3-carboxylic acid.

(C): 1-Ethyl-7-[3-(ethylamino)methyl]-1-pyrolidinyl-6,8-difluoro-1,4-dihydro-4-oxo-3-quinolinecarboxylic acid in Example 11 in J.P. No. 67269/1984.

| | A | B | C | Compound (1-A-2) of Example 1 | Compound (1-B-2) of Example 2 | Compound of Example 3 | Compound of Example 4 |
|---|---|---|---|---|---|---|---|
| E. coli, NIHJ | ≦0.05 | ≦0.05 | ≦0.05 | ≦0.05 | ≦0.05 | ≦0.05 | ≦0.05 |
| Sh. flexneri, 2a5503 | ≦0.05 | 0.10 | ≦0.05 | ≦0.05 | ≦0.05 | ≦0.05 | ≦0.05 |
| Pr. vulgaris, 3167 | 0.10 | ≦0.05 | 0.20 | 0.10 | ≦0.05 | 0.20 | ≦0.05 |
| Pr. mirabilis, IF03849 | ≦0.05 | ≦0.05 | 0.39 | 0.10 | ≦0.05 | 0.20 | 0.20 |
| Ser. marcescens, 13001 | 0.10 | ≦0.05 | 0.20 | 0.20 | ≦0.05 | 0.20 | 0.10 |
| Ps. aeruginosa, 2063 | 0.39 | 0.20 | 0.78 | 0.78 | 0.20 | 0.39 | 0.20 |
| Ps. aeruginosa, 2128 | 0.20 | 0.20 | 0.39 | 0.20 | ≦0.05 | 0.20 | 0.10 |
| Ps. cepacia, IID1340 | 0.78 | 1.56 | 1.56 | 0.78 | 0.39 | 1.56 | 0.78 |
| Ps. maltophilia, IID1275 | 0.39 | 0.20 | 0.78 | 0.20 | 0.10 | 0.78 | 0.39 |
| S. aureus, 209P | ≦0.05 | ≦0.05 | 0.10 | 0.10 | ≦0.05 | ≦0.05 | ≦0.05 |
| S. epidermidis, 56500 | ≦0.05 | ≦0.05 | 0.39 | 0.10 | ≦0.05 | 0.20 | ≦0.05 |
| Str. pyogenes, G-36 | 0.10 | 0.10 | 0.78 | 0.10 | ≦0.05 | 0.39 | ≦0.05 |
| Str. faecalis, ATCC 19433 | 0.10 | 0.10 | 0.39 | 0.10 | ≦0.05 | 0.39 | ≦0.05 |
| | Compound of Example 5 | Compound of Example 6 | Compound of Example 7 | Compound of Example 8 | Compound of Example 9 | Compound of Example 10 | |
| E. coli, NIHJ | ≦0.05 | ≦0.05 | ≦0.05 | ≦0.05 | ≦0.05 | ≦0.05 | |
| Sh. flexneri, 2a5503 | ≦0.05 | ≦0.05 | ≦0.05 | ≦0.05 | ≦0.05 | ≦0.05 | |
| Pr. vulgaris, 3167 | ≦0.05 | 0.10 | ≦0.05 | 0.10 | ≦0.05 | 0.10 | |

-continued

| | | | | | | |
|---|---|---|---|---|---|---|
| Pr. mirabilis, IF03849 | 0.39 | 0.20 | ≦0.05 | 0.39 | 0.10 | 0.20 |
| Ser. marcescens, 13001 | 0.20 | 0.20 | 0.10 | 0.39 | ≦0.05 | 0.20 |
| Ps. aeruginosa, 2063 | 0.78 | 0.39 | 0.20 | 1.56 | 0.78 | 1.56 |
| Ps. aeruginosa, 2128 | 0.20 | 0.20 | 0.10 | 0.39 | 0.20 | 0.39 |
| Ps. cepacia, IID1340 | 1.56 | 0.78 | 0.78 | 1.56 | 0.39 | 1.56 |
| Ps. maltophilia, IID1275 | 0.39 | 0.20 | 0.20 | 0.78 | 0.10 | 0.39 |
| S. aureus, 209P | ≦0.05 | ≦0.05 | ≦0.05 | 0.10 | ≦0.05 | ≦0.05 |
| S. epidermidis, 56500 | ≦0.05 | 0.10 | ≦0.05 | 0.20 | ≦0.05 | 0.10 |
| Str. pyogenes, G-36 | 0.39 | 0.20 | ≦0.05 | 0.78 | ≦0.05 | ≦0.05 |
| Str. faecalis, ATCC 19433 | 0.20 | 0.20 | ≦0.05 | 0.39 | 0.10 | ≦0.05 |

| | Compound of Example 11 | Compound of Example 12 | Compound of Example 13 | Compound of Example 14 | Compound of Example 15 | Compound of Example 16 |
|---|---|---|---|---|---|---|
| E. coli, NIHJ | ≦0.05 | ≦0.05 | ≦0.05 | ≦0.05 | ≦0.05 | ≦0.05 |
| Sh. flexneri, 2a5503 | ≦0.05 | ≦0.05 | ≦0.05 | ≦0.05 | ≦0.05 | ≦0.05 |
| Pr. vulgaris, 3167 | ≦0.05 | 0.20 | 0.10 | 0.20 | 0.10 | 0.20 |
| Pr. mirabilis, IF03849 | 0.10 | 0.39 | 0.39 | 0.20 | 0.20 | 0.39 |
| Ser. marcescens, 13001 | 0.10 | 0.39 | 0.20 | 0.39 | 0.20 | 0.39 |
| Ps. aeruginosa, 2063 | 0.78 | 1.56 | 0.39 | 3.13 | 0.39 | 1.56 |
| Ps. aeruginosa, 2128 | 0.20 | 0.39 | 0.20 | 0.39 | 0.20 | 0.39 |
| Ps. cepacia, IID1340 | 0.78 | 1.56 | 0.78 | 1.56 | 0.39 | 0.78 |
| Ps. maltophilia, IID1275 | 0.10 | 0.39 | 0.20 | 0.39 | 0.20 | 0.39 |
| S. aureus, 209P | ≦0.05 | ≦0.05 | ≦0.05 | 0.20 | ≦0.05 | ≦0.05 |
| S. epidermidis, 56500 | ≦0.05 | 0.10 | ≦0.05 | 0.20 | ≦0.05 | 0.20 |
| Str. pyogenes, G-36 | ≦0.05 | 0.10 | 0.10 | 0.10 | ≦0.05 | 0.20 |
| Str. faecalis, ATCC 19433 | ≦0.05 | 0.10 | 0.20 | 0.10 | 0.20 | 0.39 |

| | Compound of Example 17 | Compound of Example 18 | Compound of Example 19 | Compound of Example 20 | Compound of Example 21 | Compound of Example 22 |
|---|---|---|---|---|---|---|
| E. coli, NIHJ | ≦0.05 | ≦0.05 | ≦0.05 | ≦0.05 | ≦0.05 | ≦0.05 |
| Sh. flexneri, 2a5503 | ≦0.05 | ≦0.05 | ≦0.05 | ≦0.05 | ≦0.05 | ≦0.05 |
| Pr. vulgaris, 3167 | 0.10 | 0.10 | ≦0.05 | ≦0.05 | ≦0.05 | ≦0.05 |
| Pr. mirabilis, IF03849 | 0.20 | 0.20 | 0.10 | 0.10 | 0.10 | 0.10 |
| Ser. marcescens, 13001 | 0.10 | 0.20 | ≦0.05 | 0.10 | ≦0.05 | 0.10 |
| Ps. aeruginosa, 2063 | 0.39 | 0.39 | 0.20 | 0.39 | 0.20 | 0.39 |
| Ps. aeruginosa, 2128 | 0.20 | 0.20 | ≦0.05 | 0.20 | 0.10 | 0.20 |
| Ps. cepacia, IID1340 | 0.78 | 0.39 | 0.39 | 0.39 | 0.20 | 0.20 |
| Ps. maltophilia, IID1275 | 0.39 | 0.20 | 0.20 | 0.20 | ≦0.05 | 0.20 |
| S. aureus, 209P | ≦0.05 | ≦0.05 | ≦0.05 | ≦0.05 | ≦0.05 | ≦0.05 |
| S. epidermidis, 56500 | 0.10 | ≦0.05 | ≦0.05 | ≦0.05 | ≦0.05 | ≦0.05 |
| Str. pyogenes, G-36 | 0.10 | 0.39 | 0.20 | ≦0.05 | ≦0.05 | 0.20 |
| Str. faecalis, ATCC 19433 | 0.10 | 0.20 | 0.10 | ≦0.05 | ≦0.05 | 0.20 |

Water-solubility and acute toxicity

The water-solubility and acute toxicity of the compounds of the present invention and the comparative compounds, were measured. The results obtained are shown hereunder. The water-solubility was measured by the following method.

(i) Preparation of standard solution

About 400 μg of the sample to be measured was accurately weighed (the weight was defined as W μg, and 0.1N NaOH solution was added thereto to bring the whole volume to 50 ml. The UV absorbance of a given amount of the solution was measured and the measured absorbance was defined as $A_1$.

(ii) Preparation of sample to be measured

Distilled water was added to the sample to be measured (fine powder) in such amount that the sample was not completely dissolved but suspended, and then the suspension was vigorously agitated at room temperature (between 23° and 26° C.) for 30 minutes. Insoluble matter of the sample was removed therefrom by filtration, after which 3 ml sample of the filtrate (saturated aqueous solution of the sample) was taken. 3 ml of 0.2N NaOH solution was added to the filtrate sample to bring the total volume to 6 ml (i.e. the filtrate was diluted to 50% concentration.) To 1 ml of the resulting solution, 0.1N NaOH solution was futher added to bring the total volume to 25 ml (2% concentration). In this connection, degree of dilution was occasionally changed, depending on degree of UV absorbance. The UV absorbance of the given amount of the solution was measured and the resulting absorbance was defined to as $A_2$. Where the number of dilution is N, water-solubility (s) is obtained from the following equation:

$$S = \frac{W \cdot A_2}{50 \cdot A_1} \times N(\mu g/ml \cdot H_2O)$$

| | Compound of the present invention | | | Comparative compound | | |
|---|---|---|---|---|---|---|
| | Compound of example | Compound of example | Compound of example | Compound A | Compound B | Compound C |
| Water solubility (μg/ml) | 710 | 200 | 2000 | 40 | 80 | 400 |
| Acute toxicity to mouse* | 1/5 | 0/5 | 1/5 | 3/5 | 2/5 | 0/5 |

*200 mg/kg; i.v, (deaths/total number)

As is obvious from the above results, the anti-microbial agents of the present invention have high water-solubility as well as low toxicity.

Since not only N-cyclopropyl derivative (example 2, isomer B) but also $N_1$-ethyl derivative (example 4), which are 3-(2-aminoethyl) pyrrolidine derivatives, show extremely strong anti-microbial activity against Gram-negative and Gram-positive microorganisms, it can be predicted that analog thereof has naturally strong anti-microbial activity and the analog is also expected to be useful as a pharmaceutical compound.

Absorption after oral administration

The compounds of the present invention and the comparative compound were orally given to rats (one group: 5 rats) at a dose of 20 mg/kg to measure the oral absorption of the compounds. The concentration of the compound in the blood of the rat was measured at 15 minutes, 30 minutes, and 1, 2, 3, 4, and 6 hours after administration.

Serum half lives (T1/2) were calculated as $0.693/K_{el}$, where $K_{el}$ is the elimination rate constant determined by linear regression analysis of the natural logarithm of serum concentration-time data. The area under the serum concentration-versus time curve from zero to 6 h ($AUC_{0-6H}$) was calculated by the trapezoidal method. The results obtained are as follows:

|  |  | Cmax (μg/ml.1H) | T½ (min.) | AUC0-6H (μg.h/ml) |
|---|---|---|---|---|
| Compound of the present invention | Compound of Example 7 | 2.21 | 120.6 | 6.31 |
|  | Compound of Example 11 | 2.10 | 135.9 | 6.43 |
|  | Compound of Example 13 | 2.14 | 144.6 | 7.95 |
| Comparative compound B |  | 1.37 | 93.0 | 3.61 |

As is obvious from the above data, the compounds of the present invention are superior to the comparative example in terms of oral absorption.

What is claimed is:
1. 1-benzyloxycarbonyl-3-(1-tert-butoxycarbonylaminoethyl)pyrrolidine.
2. 3-(1-tert-butoxycarbonylaminoethyl)-pyrrolidine.
3. 3-(1-tert-butoxycarbonylaminopropyl)-pyrrolidine.
4. A compound as set forth in anyone of claim 1 wherein said compound is a single stereo-isomer.
5. A compound as set forth in anyone of claim 2 wherein said compound is a single stereo-isomer.
6. A compound as set forth in anyone of claim 3 wherein said compound is a single stereo-isomer.

* * * * *